(12) United States Patent
Hartz et al.

(10) Patent No.: US 8,436,000 B2
(45) Date of Patent: May 7, 2013

(54) SUBSTITUTED CARBAMATE DERIVATIVES AS MODULATORS OF CORTICOTROPIN-RELEASING FACTOR RECEPTOR ACTIVITY

(75) Inventors: Richard A. Hartz, Middletown, CT (US); Vijay T. Ahuja, Middletown, CT (US); John E. Macor, Guilford, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 227 days.

(21) Appl. No.: 13/055,885

(22) PCT Filed: Jul. 29, 2009

(86) PCT No.: PCT/US2009/052078
§ 371 (c)(1),
(2), (4) Date: Jan. 25, 2011

(87) PCT Pub. No.: WO2010/014687
PCT Pub. Date: Feb. 4, 2010

(65) Prior Publication Data
US 2011/0124662 A1    May 26, 2011

Related U.S. Application Data

(60) Provisional application No. 61/085,243, filed on Jul. 31, 2008.

(51) Int. Cl.
*A61K 31/497* (2006.01)

(52) U.S. Cl.
USPC .................................. 514/255.05; 544/405

(58) Field of Classification Search ................... 544/405
See application file for complete search history.

(56) References Cited

FOREIGN PATENT DOCUMENTS
WO   WO 2004/017963   3/2004

*Primary Examiner* — Brian McDowell
(74) *Attorney, Agent, or Firm* — James Epperson

(57) ABSTRACT

The disclosure provides compounds of formula (I), including their salts, as well as compositions and methods of using the compounds. The compounds are CRF receptor antagonists and may be useful for treating disorders associated with abnormal CRF levels or aberrant functioning of CRF receptors.

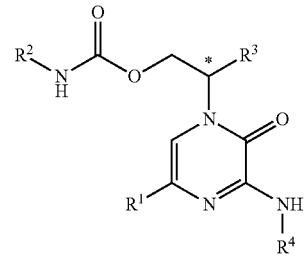

(I)

12 Claims, No Drawings

SUBSTITUTED CARBAMATE DERIVATIVES AS MODULATORS OF CORTICOTROPIN-RELEASING FACTOR RECEPTOR ACTIVITY

CROSS-REFERENCE TO RELATED APPLICATIONS

This application claims the benefit of U.S. provisional application Ser. No. 61/085,243 filed Jul. 31, 2008.

BACKGROUND OF THE INVENTION

Corticotropin releasing factor ("CRF"), acting through the CRF-1 receptor, is a primary mediator of stress- and anxiety-related physiological responses in humans and other mammals. Antagonists of the CRF-1 receptor, both peptides (J. Gulyas, et al., *Proc. Natl. Acad. Sci. U.S.A.*, 92: 10575-10579 (1995) and small molecules (J. R. McCarthy, et al., *Curr. Pharm. Design*, 5: 289-315 (1999), have demonstrated the ability to ameliorate the effects of stressful stimuli in several animal models. CRF antagonists have been suggested to affect both anxiety and depression as well as other stress related afflictions. See F. Holsboer, *J. Psychiatr. Res.* 33(3): 181-214 (1999); S. C. Heinrichs, Y. Tache, *Exp. Opin. Invest. Drugs* 10(4): 647-659 (2001); P. J. Gilligan, et al., *J. Med. Chem.*, 43: 1641-1660 (2000); and J. R. McCarthy, et al., *Ann. Rep. Med. Chem.*, 34: 11-20 (1999). As such, there is a continuing need to discover novel small molecule CRF antagonists in order to treat a wide variety of human disorders including affective disorders and other stress-related illnesses.

The invention provides technical advantages, for example, the compounds are novel and are effective at modulating CRF receptors. Additionally, the compounds provide advantages for pharmaceutical uses, for example, with regard to one or more of their mechanism of action, binding, inhibition efficacy, target selectivity, solubility, safety profiles, or bioavailability.

DESCRIPTION OF THE INVENTION

The disclosure generally relates to the novel compounds of formula I, including their salts, which have use in treating affective disorders. The disclosure also relates to compositions of these compounds and methods of treating disorders using these compounds.

One aspect of the invention is a compound of Formula I

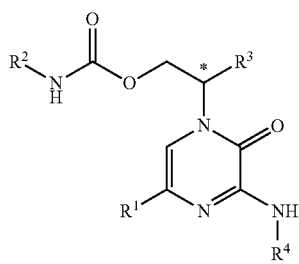

I where:
$R^1$ is hydrogen, halo, cyano, or alkyl;
$R^2$ is alkyl or haloalkyl;
or $R^2$ is phenyl, pyridinyl, pyrimidinyl, pyridazinyl, or triazinyl, and is substituted with 0-3 substituents independently selected from the group consisting of halo, cyano, alkyl, alkoxy, haloalkyl, and haloalkoxy;
$R^3$ is hydrogen, alkyl, alkenyl, alkynyl, cycloalkyl, (cycloalkyl)alkyl, haloalkyl, alkoxyalkyl, or (haloalkoxy)alkyl;
$R^4$ is phenyl, pyridinyl, pyrimidinyl, pyridazinyl, or triazinyl and is substituted with 0-3 substituents independently selected from the group consisting of halo, alkyl, alkoxy, haloalkyl, and haloalkoxy; and
the carbon bearing the asterisk is of the (R) or (S) configuration;
or a pharmaceutically acceptable salt thereof.

Another aspect of the invention is a compound of formula I where $R^1$ is halo or cyano; $R^2$ is alkyl or is pyridinyl substituted with 0-3 substituents independently selected from the group consisting of halo, cyano, alkyl, and alkoxy; $R^3$ is cycloalkyl; $R^4$ is pyridinyl substituted with 0-3 substituents independently selected from the group consisting of alkyl, alkoxy, and haloalkoxy; and the carbon bearing the asterisk is of the (S) configuration; or a pharmaceutically acceptable salt thereof.

Another aspect of the invention is a compound of formula I where $R^1$ is chloro or cyano; $R^2$ is ethyl, propyl, butyl, phenyl, cyanophenyl, chlorophenyl, dichlorophenyl, pyridinyl, (methyl)(methoxy)pyridinyl, (dimethyl)(methoxy)pyridinyl, or (dimethyl)(ethoxy)pyridinyl; $R^3$ is cyclopropyl; $R^4$ is (dimethyl)(methoxy)pyridinyl or (dimethyl)(difluoromethoxy)pyridinyl; and the carbon bearing the asterisk is of the (S) configuration; or a pharmaceutically acceptable salt thereof.

Another aspect of the invention is a compound of Formula I where $R^1$ is hydrogen, chloro, bromo, cyano, or methyl.

Another aspect of the invention is a compound of Formula I where $R^2$ is alkyl.

Another aspect of the invention is a compound of Formula I where $R^2$ is phenyl or pyridinyl and is substituted with 0-3 substituents independently selected from halo, cyano, alkyl, alkoxy, haloalkyl, and haloalkoxy.

Another aspect of the invention is a compound of Formula I where $R^3$ is alkyl, cycloalkyl, or alkoxyalkyl.

Another aspect of the invention is a compound of Formula I where $R^3$ is cycloalkyl.

Another aspect of the invention is a compound of Formula I where $R^3$ is cyclopropyl.

Another aspect of the invention is a compound of Formula I where $R^4$ is pyridinyl and is substituted with 0-3 substituents independently selected from alkyl, alkoxy, and haloalkoxy.

Another aspect of the invention is a compound of Formula I where $R^4$ is pyridinyl and is substituted with 3 substituents independently selected from alkyl, alkoxy, and haloalkoxy.

Another aspect of the invention is a compound of Formula I where $R^4$ is pyridinyl and is substituted with 3 substituents independently selected from methyl, methoxy, and difluoromethoxy.

Another aspect of the invention is a compound where the carbon bearing the asterisk is of the (S) configuration.

For a compound of Formula I, the scope of any instance of a variable substituent, including $R^1$, $R^2$, $R^3$, and $R^4$, can be used independently with the scope of any other instance of a variable substituent. As such, the invention includes combinations of the different aspects.

Unless specified otherwise, these terms have the following meanings. "Alkyl" means a straight or branched alkyl group composed of 1 to 6 carbons. "Alkenyl" means a straight or branched alkyl group composed of 2 to 6 carbons with at least one double bond. "Alkynyl" means a straight or branched alkyl group composed of 2 to 6 carbons with at least one triple bond. "Cycloalkyl" means a monocyclic ring system composed of 3 to 7 carbons. "Haloalkyl" and "haloalkoxy" include all halogenated isomers from monohalo to perhalo. Terms with a hydrocarbon moiety (e.g. alkoxy) include straight and branched isomers for the hydrocarbon portion. Parenthetic and multiparenthetic terms are intended to clarify bonding relationships to those skilled in the art. For example, a term such as ((R)alkyl) means an alkyl substituent further substituted with the substituent R.

The invention includes all pharmaceutically acceptable salt forms of the compounds. Pharmaceutically acceptable salts are those in which the counter ions do not contribute significantly to the physiological activity or toxicity of the compounds and as such function as pharmacological equivalents. These salts can be made according to common organic techniques employing commercially available reagents. Some anionic salt forms include acetate, acistrate, besylate, bromide, chloride, citrate, fumarate, glucouronate, hydrobromide, hydrochloride, hydroiodide, iodide, lactate, maleate, mesylate, nitrate, pamoate, phosphate, succinate, sulfate, tartrate, tosylate, and xinofoate. Some cationic salt forms include ammonium, aluminum, benzathine, bismuth, calcium, choline, diethylamine, diethanolamine, lithium, magnesium, meglumine, 4-phenylcyclohexylamine, piperazine, potassium, sodium, tromethamine, and zinc.

Some of the compounds of the invention possess asymmetric carbon atoms (see, for example, the compounds below). The invention includes all stereoisomeric forms, including enantiomers and diastereomers as well as mixtures of stereoisomers such as racemates. Methods of making and separating stereoisomers are known in the art.

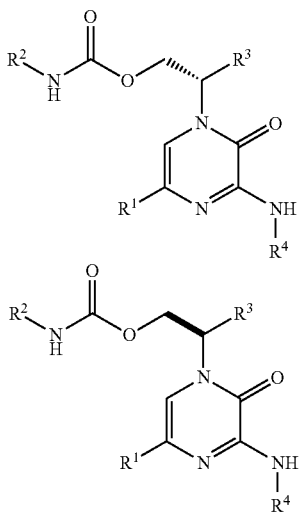

The invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds may have a variety of potential uses, for example as standards and reagents in determining biological activity. In the case of stable isotopes, such compounds may have the potential to favorably modify biological, pharmacological, or pharmacokinetic properties.

Synthetic Methods

The compounds may be made by methods known in the art including those described below and including variations within the skill of the art. Some reagents and intermediates are known in the art. Other reagents and intermediates can be made by methods known in the art using readily available materials. The variables (e.g. numbered "R" substituents) used to describe the synthesis of the compounds are intended only to illustrate how to make the compounds and are not to be confused with variables used in the claims or in other sections of the specification. The following methods are for illustrative purposes and are not intended to limit the scope of the invention.

Abbreviations used in the schemes generally follow conventions used in the art. Chemical abbreviations used in the specification and examples are defined as follows: "NaHMDS" for sodium bis(trimethylsilyl)amide; "DMF" for N,N-dimethylformamide; "MeOH" for methanol; "NBS" for N-bromosuccinimide; "Ar" for aryl; "TFA" for trifluoroacetic acid; "LAH" for lithium aluminum hydride; "BOC", "DMSO" for dimethylsulfoxide; "h" for hours; "rt" for room temperature or retention time (context will dictate); "min" for minutes; "EtOAc" for ethyl acetate; "THF" for tetrahydrofuran; "EDTA" for ethylenediaminetetraacetic acid; "Et$_2$O" for diethyl ether; "DMAP" for 4-dimethylaminopyridine; "DCE" for 1,2-dichloroethane; "ACN" for acetonitrile; "DME" for 1,2-dimethoxyethane; "HOBt" for 1-hydroxybenzotriazole hydrate; "DIEA" for diisopropylethylamine, "Nf" for $CF_3(CF_2)_3SO_2$—; and "TMOF" for trimethylorthoformate.

The route to intermediates of Formula 10 begin with conversion of commercially available α-methoxy acid 2 to amide 3, followed by addition of a Grignard reagent which affords ketone 4. Reductive amination, followed by protection of the amine as the (benzyloxy)carbamate, provides racemic intermediate 5. Separation of the enantiomers by chromatography can generate the single enantiomer 6, if isolation of a single enantiomer is desired. Deprotection under acidic conditions provides (S)-amine 7. Alkylation of amine 7 with chloroacetonitrile provides α-amino nitrile 8. Treatment of the nitrile 8 with oxalyl chloride provides dichloropyrazinone 9. Coupling of the dichloropyrazinone 9 with amines $R^4NH_2$ can be achieved in the presence of NaHMDS to provide compounds of Formula 10. When $R^1$=CN, the chloride can be replaced with cyano by coupling with zinc cyanide in the presence of a palladium catalyst such as Pd$_2$(dba)$_3$. Alternatively, the cyclization reaction to form the pyrazinone ring can be carried out in the presence of oxalyl bromide to furnish the dibromopyrazinone. Compound 10, when $R^1$=Br, can then either be coupled with zinc cyanide in the presence of a palladium catalyst such as Pd$_2$(dba)$_3$ to furnish compounds of Formula 10 where $R^1$=CN or compound 10, when $R^1$=Br, can be coupled with methylboronic acid in the presence of a palladium catalyst to furnish compounds of Formula 10 where $R^1$=Me.

Scheme 1

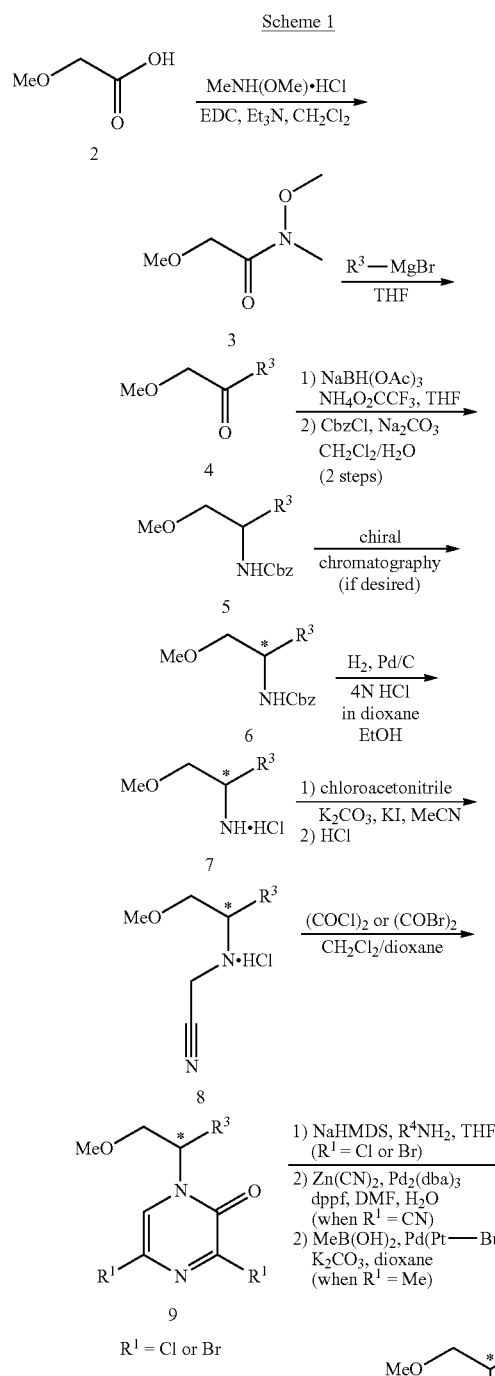

Scheme 2

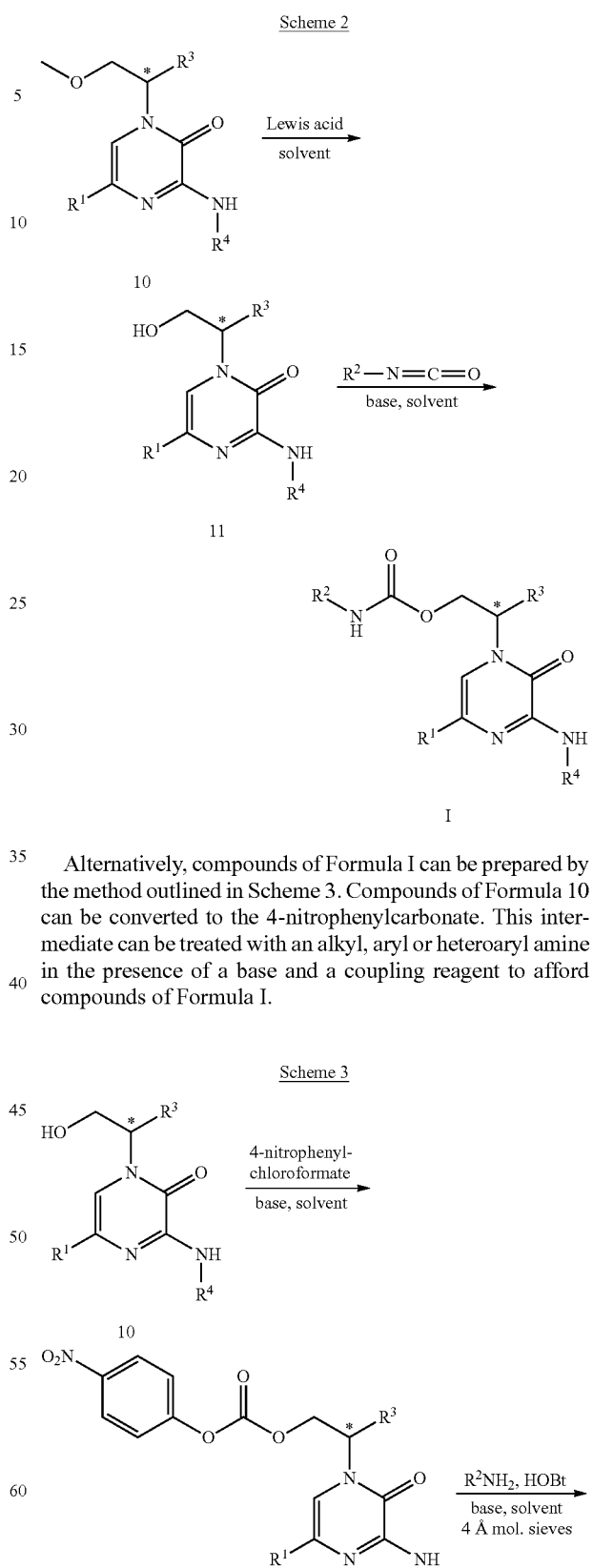

Compounds of Formula 10 can be demethylated, for example using a Lewis acid by methods known in the art to give compounds of Formula 11 (Scheme 2). The resulting intermediate alcohol can be treated with an isocyanate in conjunction with a base to afford compounds of Formula I.

Alternatively, compounds of Formula I can be prepared by the method outlined in Scheme 3. Compounds of Formula 10 can be converted to the 4-nitrophenylcarbonate. This intermediate can be treated with an alkyl, aryl or heteroaryl amine in the presence of a base and a coupling reagent to afford compounds of Formula I.

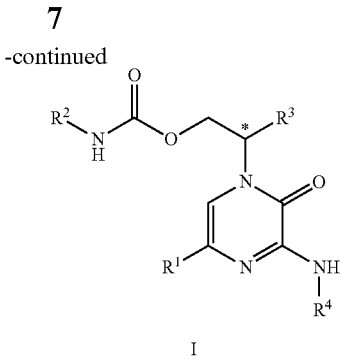

I

Biological Methods

CRF₁ Binding Assay.

Frozen rat frontal cortex was thawed rapidly in assay buffer containing 50 mM Hepes (pH 7.0 at 23° C.), 10 mM $MgCl_2$, 2 mM EGTA, 1 μg/ml aprotinin, 1 μg/ml leupeptin, 1 Mg/ml pepstatin A, 0.005% Triton X-100, 10 U/ml bacitracin and 0.1% ovalbumin and homogenized. The suspension was centrifuged at 32000×g for 30 minutes. The resulting supernatant was discarded and the pellet resuspended by homogenization in assay buffer and centrifuged again. The supernatant was discarded and the pellet resuspended by homogenization in assay buffer and frozen at −70° C. On the day of the experiment aliquots of the homogenate were thawed quickly and 25 μg/well added to 150 μM $^{125}$I-ovine-CRF ($^{125}$I-o-CRF) and drugs in a total volume of 100 μl assay buffer. The assay mixture was incubated for 2 hr at 21° C. Bound and free radioligand were then separated by rapid filtration using glass fiber filters (Whatman GF/B, pretreated with 0.3% PEI (polyethylenimine)) on a Brandel Cell Harvester. Filters were then washed multiple times with ice cold wash buffer (PBS w/o $Ca^{2+}$ and $Mg^{2+}$, 0.01% Triton X-100; pH 7.0 at 23° C.). Non-specific binding was defined using 1 μM DMP696, a CRF₁ selective antagonist [Li, Y-W. et al., *CNS Drug Reviews* 11: 21-52, (2005)]. Filters were then counted in a Wallac Wizard gamma counter. $IC_{50}$ values were determined in a five point (five drug concentrations) or ten point (ten drug concentrations) competition assay using non-linear regression by Microsoft Excel-fit. Rat frontal cortex was obtained from Analytical Biological Services, Inc. (Wilmington, Del.). $^{125}$I-ovine-CRF (2200 Ci/mmol) was obtained from PerkinElmer Life Sciences, Inc. (Boston, Mass.). Binding affinity for some compounds are shown in Table 1.

TABLE 1

| Example | CRF $IC_{50}$ (nM) |
|---|---|
| 1 | A |
| 2 | A |
| 3 | A |
| 4 | A |
| 5 | A |
| 6 | A |
| 7 | A |
| 8 | 4.74 |
| 9 | A |
| 10 | A |
| 11 | 15.9 |
| 12 | A |
| 13 | A |
| 14 | 0.74 |
| 15 | A |

A = 0.1-100 nM; B = 100-1000 nM.

Functional Assay (Y-79 cells).

Human Y-79 retinoblastoma cells were suspended in assay buffer (Hank's Balanced Salt Solution containing 2 mM $CaCl_2$, 5 mM $MgCl_2$, 20 mM HEPES, 1 mM IBMX) and plated at 20,000 cells/well in a 96-well black plate. CRF antagonists (typically 0.01 to 10,000 nM) were then added to wells as needed and allowed to equilibrate with the cells for 30 minutes at 37° C. CRF (1 nM; CRF $EC_{50}$=1.11±0.14 nM, n=6), dissolved in assay buffer+0.1% BSA, was then added to the wells (30 minutes at 37° C.) to stimulate the production of cAMP. The reaction was terminated by the addition of a lysis solution containing homogeneous time resolved florescence (HTRF) cAMP XL665 conjugate followed by HTRF anti-cAMP cryptate conjugate (CIS bio International). Plates were subsequently incubated at room temperature for 1 hour prior to reading the time-resolved fluorescence signal. The amount of cAMP produced was estimated from a standard curve prepared using known concentrations of cAMP. The percentage inhibition of CRF-induced cAMP production was determined for each compound (triplicate determinations). The effect of CRF antagonists on basal cAMP production (i.e. in the absence of CRF) was also determined.

In vivo Biological Assay.

Several assays for in vivo activity of compounds are accepted within the art. Illustrative of these tests includes the Acoustic Startle Assay, the Stair Climbing Test, and the Chronic Administration Assay. These and other models useful for the testing of compounds of the present invention have been outlined in C. W. Berridge and A. J. Dunn, *Brain Research Reviews*, 15:71 (1990).

Pharmaceutical Compositions and Methods of Treatment

Compounds of formula I are CRF receptor antagonists and may have use in treating conditions related to abnormal levels of CRF, for example in patients suffering from affective disorders including depression or anxiety.

Accordingly, another aspect of the invention is a method for treating affective disorders.

Another aspect of the invention is a method for treating the affective disorder anxiety.

Another aspect of the invention is a method for treating the affective disorder depression.

The compounds of this invention are generally given as pharmaceutical compositions comprised of a therapeutically effective amount of a compound or its pharmaceutically acceptable salt and a pharmaceutically acceptable carrier and may contain conventional excipients. Pharmaceutically acceptable carriers are those conventionally known carriers having acceptable safety profiles. Compositions encompass all common solid and liquid forms including for example capsules, tablets, losenges, and powders as well as liquid suspensions, syrups, elixers, and solutions. Compositions are made using common formulation techniques, and conventional excipients (such as binding and wetting agents) and vehicles (such as water and alcohols) are generally used for compositions. See, for example, *Remington's Pharmaceutical Sciences*, Mack Publishing Company, Easton, Pa., 17th edition, 1985.

Solid compositions are normally formulated in dosage units and compositions providing from about 1 to 1000 mg of the active ingredient per dose are preferred. Some examples of dosages are 1 mg, 10 mg, 100 mg, 250 mg, 500 mg, and 1000 mg. Generally, other agents will be present in a unit range similar to agents of that class used clinically. Typically, this is 0.25-1000 mg/unit.

Liquid compositions are usually in dosage unit ranges. Generally, the liquid composition will be in a unit dosage range of 1-100 mg/mL. Some examples of dosages are 1 mg/mL, 10 mg/mL, 25 mg/mL, 50 mg/mL, and 100 mg/mL. Generally, other agents will be present in a unit range similar to agents of that class used clinically. Typically, this is 1-100 mg/mL.

Compounds of this invention can be administered to treat these disorders by means that produce contact of the active agent with the agent's site of action in the body of a patient. The compounds can be administered by any conventional means available for use in conjunction with pharmaceuticals either as individual therapeutic agent or in combination of therapeutic agents. They can be administered alone, but will generally be administered with a pharmaceutical carrier selected on the basis of the chosen route of administration and standard pharmaceutical practice.

The invention encompasses all conventional modes of administration; oral and parenteral methods are preferred. Generally, the dosing regimen will be similar to other agents used clinically. Typically, the daily dose will be 0.001-100 mg/kg body weight daily. Generally, more compound is required orally and less parenterally. The specific dosing regime, however, will be determined by a physician using sound medical judgment.

"Therapeutically effective" means the amount of agent required to provide a meaningful patient benefit as understood by practitioners in the field of psychological, neurological, or affective disorders. A therapeutically effective amount is that which is needed to provide a meaningful patient benefit.

"Treatment," "therapy," "regimen," and related terms are used as understood by medical practitioners in the art.

"Patient" means a person suitable for therapy as understood by medical practitioners in the art.

DESCRIPTION OF SPECIFIC EMBODIMENTS

Abbreviations used in the schemes generally follow conventions used in the art. Chemical abbreviations used in the specification and Examples are defined as follows: "NaHMDS" for sodium bis(trimethylsilyl)amide; "DMF" for N,N-dimethylformamide; "MeOH" for methanol; "NBS" for N-bromosuccinimide; "Ar" for aryl; "TFA" for trifluoroacetic acid; "LAH" for lithium aluminum hydride; "BOC", "DMSO" for dimethylsulfoxide; "h" for hours; "rt" for room temperature or retention time (context will dictate); "min" for minutes; "EtOAc" for ethyl acetate; "THF" for tetrahydrofuran; "EDTA" for ethylenediaminetetraacetic acid; "Et$_2$O" for diethyl ether; "DMAP" for 4-dimethylaminopyridine; "DCE" for 1,2-dichloroethane; "ACN" for acetonitrile; "DME" for 1,2-dimethoxyethane; "HOBt" for 1-hydroxybenzotriazole hydrate; "DIEA" for diisopropylethylamine, "Nf" for CF$_3$(CF$_2$)$_3$SO$_2$—; and "TMOF" for trimethylorthoformate.

Abbreviations as used herein, are defined as follows: "1×" for once, "2×" for twice, "3×" for thrice, "° C." for degrees Celsius, "eq" for equivalent or equivalents, "g" for gram or grams, "mg" for milligram or milligrams, "L" for liter or liters, "mL" for milliliter or milliliters, "µL" for microliter or microliters, "N" for normal, "M" for molar, "mmol" for millimole or millimoles, "min" for minute or minutes, "h" for hour or hours, "rt" for room temperature, "RT" for retention time, "atm" for atmosphere, "psi" for pounds per square inch, "conc." for concentrate, "sat" or "sat'd" for saturated, "MW" for molecular weight, "mp" for melting point, "ee" for enantiomeric excess, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "RP HPLC" for reverse phase HPLC, "TLC" or "tlc" for thin layer chromatography, "NMR" for nuclear magnetic resonance spectroscopy, "$^1$H" for proton, "δ" for delta, "s" for singlet, "d" for doublet, "t" for triplet, "q" for quartet, "m" for multiplet, "br" for broad, "Hz" for hertz, and "α", "β", "R", "S", "E", and "Z" are stereochemical designations familiar to one skilled in the art.

Example 1

(S)-2-(5-Chloro-3-(6-methoxy-2,5-dimethylpyridin-3-ylamino)-2-oxopyrazin-1(2H)-yl)-2-cyclopropyl-ethyl phenylcarbamate

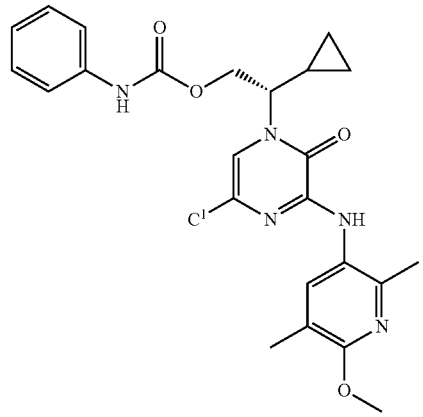

Part A. N,2-Dimethoxy-N-methylacetamide

Triethylamine (115 mL) was added to a solution of methoxyacetic acid (35.0 g, 389 mmol) in CH$_2$Cl$_2$ (1200 mL) at room temperature. N,O-dimethylhydroxylamine hydrochloride (45.5 g, 467 mmol) was added, and after stirring for 5 min, the suspension was cooled to 0° C. Ethyl diazocarboxylate (EDC) (81.7 g, 428 mmol) was then added and the reaction mixture was stirred overnight while allowing it to warm to room temperature. The mixture was poured into a separatory funnel and diluted with CH$_2$Cl$_2$ (500 mL). The organic layer was washed with 1 N HCl (2×300 mL), saturated aqueous NaHCO$_3$ solution (2×300 mL), and brine (300 mL). The resulting solution was dried over MgSO$_4$, filtered and concentrated in vacuo. The product was purified by column chromatography on a short column of silica gel (5% methanol in CH$_2$Cl$_2$) to afford N,2-dimethoxy-N-methylacetamide (33.2 g, 64% yield) as a colorless oil: $^1$H NMR (400 MHz, CDCl$_3$) δ 4.20 (s, 2H), 3.67 (s, 3H), 3.45 (s, 3H), 3.17 (s, 3H); $^{13}$C NMR (100 MHz, CDCl$_3$) δ 173.0, 69.7, 69.4, 61.4, 59.4; LRMS (ESI) m/e 134.1 [(M+H)$^+$, calcd for C$_5$H$_{12}$NO$_3$ 134.1].

Part B. 1-Cyclopropyl-2-methoxyethanone

Magnesium turnings (15.2 g, 632 mmol) were added to a 5-L 3-necked flask equipped with an addition funnel. The flask, funnel, and turnings were flame dried and then a reflux condenser was then placed on the flask. After the flask and contents had cooled to room temperature, diethyl ether (100 mL) was added to the flask, followed by addition of a portion of cyclopropyl bromide (5.0 mL, 7.55 g, 62.4 mmol) and several crystals of iodine. After the reaction had initiated, diethyl ether (400 mL) was added to the reaction flask. The remaining cyclopropyl bromide (87.3 g, 721 mmol) was then added slowly over 30 min with intermittent cooling of the reaction mixture with an ice-water bath. After the addition was complete and the magnesium was consumed, additional diethyl ether (700 mL) was added and the reaction mixture was cooled to 0° C. The magnetic stirrer was replaced with a mechanical stirrer and a solution of N,2-dimethoxy-N-methylacetamide (42.07 g, 316 mmol) from Part A dissolved in diethyl ether (500 mL) was added slowly over 30 min via the addition funnel. A white solid formed during this time. After the addition was complete, the cooling bath was removed and the mixture was stirred at room temperature for 1 h. The mixture was then cooled to 0° C. and the reaction was quenched by the addition of 1 N HCl (700 mL, added slowly at first). After stirring for an additional 15 min, the mixture was transferred to a separatory funnel, and the aqueous layer was extracted with ether (3×500 mL). The combined organic layers were washed with saturated aqueous $NaHCO_3$ solution (400 mL), brine (400 mL), dried over $MgSO_4$, filtered and concentrated with minimal vacuum (500 mbar). The product was purified by distillation under reduced pressure while submerging the collection flask in a dry ice/isopropanol bath to afford 1-cyclopropyl-2-methoxyethanone (29.2 g, 81% yield) as a colorless oil: bp 35-38° C., 5 mm Hg; $^1$H NMR (400 MHz, $CDCl_3$) δ 4.13 (s, 2H), 3.43 (s, 3H), 2.11-2.07 (m, 1H), 1.10-1.06 (m, 2H), 0.94-0.89 (m, 2H); GC/MS (CI) m/e 115.1 [(M+H)$^+$, calcd for $C_6H_{11}O_2$ 115.1].

Part C. Benzyl 1-cyclopropyl-2-methoxyethylcarbamate

1-Cyclopropyl-2-methoxyethanone (10.0 g, 88.0 mmol) from Part B in THF (1000 mL) was treated with ammonium trifluoroacetate (115 g, 880 mmol) and the mixture was cooled to 0° C. Sodium triacetoxyborohydride (27.9 g, 133 mmol) was added, the cooling bath was removed and the reaction mixture was gently heated at 40° C. with a warm water bath for 2 h. The mixture was cooled to room temperature and concentrated to give 1-cyclopropyl-2-methoxyethanamine which was used directly in the next step.

Crude 1-cyclopropyl-2-methoxyethanamine from the previous step was dissolved in $CH_2Cl_2/H_2O$ (300 mL/300 mL) and $Na_2CO_3$ (111.9 g, 1.06 mol) was added. The reaction mixture was placed in an ice bath and CbzCl (16.46 g, 96.78 mmol) was added via syringe. During the addition, the internal reaction mixture temperature was maintained at 15-20° C. After the addition was complete, the reaction mixture was stirred at room temperature for 2 h. The mixture was poured into a separatory funnel, diluted with $H_2O$, (300 mL), and extracted with $CH_2Cl_2$ (3×300 mL). The combined organic layers were washed with brine (300 mL), dried over $MgSO_4$, filtered and concentrated. The product was purified by column chromatography on silica gel (30% ethyl acetate in hexanes) to furnish benzyl 1-cyclopropyl-2-methoxyethylcarbamate (17.2 g, 78% yield for 2 steps) as an oil which crystallized upon standing: mp 190.5-192° C.; $^1$H NMR (400 MHz, DMSO-$d_6$) δ 7.39-7.29 (m, 5H), 7.17 (d, J=8.5 Hz, 1H), 5.00 (s, 2H), 3.36-3.34 (m, 2H), 3.23 (s, 3H), 3.19-3.14 (m, 1H), 0.85-0.79 (m, 1H), 0.43-0.37 (m, 1H), 0.35-0.22 (m, 2H), 0.20-0.16 (m, 1H); LRMS (ESI) m/e 250.3 [(M+H)$^+$, calcd for $C_{14}H_{20}NO_3$ 250.1].

Part D. (S)-Benzyl 1-cyclopropyl-2-methoxyethylcarbamate

Racemic 1-cyclopropyl-2-methoxyethylcarbamate from Part C was separated into its enantiomers by HPLC: Chiralpak AD column (10 cm×50 cm), 94% heptane/6% ethanol, 300 mL/min, λ=210 nm, 1 gram per injection, 30 min method, Peak 1 (S), Peak 2 (R) and was determined to have an optical purity>99% ee by analytical HPLC (Chiralpak AD column, 4.6×250 mm; 95% heptane/5% ethanol, 0.8 mL/min, λ=212 nm, $t_R$=15.79 min): mp 190.5-192° C.; $[α]^{25}_D$ –18.2 (c 0.500, $CHCl_3$); $^1$H NMR (400 MHz, DMSO-$d_6$) δ 7.39-7.29 (m, 5H), 7.17 (d, J=8.5 Hz, 1H), 5.00 (s, 2H), 3.36-3.34 (m, 2H), 3.23 (s, 3H), 3.19-3.14 (m, 1H), 0.85-0.79 (m, 1H), 0.43-0.37 (m, 1H), 0.35-0.22 (m, 2H), 0.20-0.16 (m, 1H); $^{13}$C NMR (100 MHz, $CDCl_3$) δ 155.6, 136.9, 128.0, 127.38, 127.34, 74.0, 64.8, 57.8, 53.5, 12.6, 2.2, 1.5; LRMS (ES$^+$) m/e 272.3 [(M+Na)$^+$, calcd for $C_{34}H_{19}NO_3Na$ 272.1].

Part E. (S)-1-Cyclopropyl-2-methoxyethanamine hydrochloride

To a solution of (S)-1-cyclopropyl-2-methoxyethylcarbamate (4.36 g, 17.5 mmol) from Part D in EtOH (80 mL) and $CHCl_3$ (3 mL) in a Parr bottle was added 4 N HCl in dioxane (5 mL) and Pd/C (476 mg, 10%, wet, Degussa type). The mixture was placed on a Parr shaker under $H_2$ atm at 45 psi for 16 h. The reaction mixture was filtered through a pad of Celite and the filtrate was concentrated then reconcentrated from hexanes (2×) to afford (S)-1-cyclopropyl-2-methoxyethanamine hydrochloride (2.65 g, 100% yield) as a white solid: mp 190-192° C.; $[α]^{25}_D$ +14.3 (c 0.446, MeOH); $^1$H NMR (400 MHz, $CDCl_3$) δ 8.41 (s br, 3H), 3.68 (d, J=5.6 Hz, 2H), 3.39 (s, 3H), 2.64-2.60 (m, 1H), 1.20-1.13 (m, 1H), 0.71-0.58 (m, 3H), 0.32-0.28 (m, 1H); $^{13}$C NMR (100 MHz, $CDCl_3$) δ 72.1, 59.2, 57.5, 10.7, 4.2, 4.1; LRMS (ESI) m/e 231.2 [(2M+H)$^+$, calcd for $C_{12}H_{27}N_2O_2$ 231.2].

Part F. (S)-2-(1-Cyclopropyl-2-methoxyethylamino) acetonitrile hydrochloride

Chloroacetonitrile (8.40 mL, 133 mmol) was added to a stirred suspension of (S)-1-cyclopropyl-2-methoxyethanamine hydrochloride (20.0 g, 133 mmol) from Part E, $K_2CO_3$ (52.0 g, 376 mmol) and KI (24.2 g, 145 mmol) in acetonitrile (300 mL) at room temperature. The mixture was stirred at 48° C. for 17 hours. The reaction mixture was then cooled to room temperature then filtered through a pad of Celite. The resulting filtrate was concentrated to a dark brown semi-solid. The solid was suspended in $CH_2Cl_2$ and purified by column chromatography on silica gel ($CH_2Cl_2$→3% methanol in $CH_2Cl_2$) to yield a brown oil (18.8 g). The oil was dissolved in $Et_2O$ (150 mL) and the solution was acidified with 2 N HCl in $Et_2O$ (100 mL) to give (S)-2-(1-cyclopropyl-2-methoxyethylamino)-acetonitrile hydrochloride (23.6 g, 93% yield) as an off-white solid: $[α]^{25}_D$ +22.9 (c 0.714, $CHCl_3$); $^1$H NMR (400 MHz, $CDCl_3$) δ 10.51 (s br, 2H), 4.39 (ABq, $J_{AB}$=16.7, Δv=24.4 Hz, 2H), 3.94 (dd, $J_{AB}$=10.6, $J_{AX}$=7.8 Hz, 1H), 3.79 (dd, $J_{BA}$ 10.8, $J_{BX}$=2.2 Hz, 1H), 3.42 (s, 3H), 2.79-2.75 (m, 1H), 1.25-1.17 (m, 1H), 0.90-0.83 (m, 1H), 0.78-0.70 (m, 2H), 0.39-0.34 (m, 1H); LRMS (ES$^+$) m/e 155.2 [(M+H)$^+$, calcd for $C_8H_{15}N_2O$ 155.1].

Part G. (S)-3,5-Dichloro-1-(1-cyclopropyl-2-methoxyethyl)pyrazin-2(1H)-one

Oxalyl chloride (54.5 mL, 624 mmol) was added dropwise to a cold (<8° C.) solution of (S)-2-(1-cyclopropyl-2-methoxyethylamino)acetonitrile hydrochloride (23.6 g, 124 mmol) from Part F in 1,4 dioxane (300 mL) and methylene chloride (200 mL). The reaction mixture was then heated at 53° C. for 19 h. The reaction mixture was cooled to room temperature and concentrated to a semi-solid then co-evaporated three times with $CH_2Cl_2$ (50 mL). The resulting brown solid was purified by column chromatography on silica gel (0→10%→20% ethyl acetate in hexanes) to afford (S)-3,5-dichloro-1-(1-cyclopropyl-2-methoxyethyl)pyrazin-2(1H)-one (22.4 g, 69% yield) as a white solid: mp 109.8-110.8° C.; $[\alpha]^{25}_D$ –88.8 (c 0.513, $CHCl_3$); $^1$H NMR (400 MHz, $CDCl_3$) δ 7.54 (s, 1H), 4.12-4.08 (m, 1H), 3.73 (dd, $J_{AB}$=10.3, $J_{AX}$=4.5 Hz, 1H), 3.62 (dd, $J_{BA}$=10.3, $J_{BX}$=3.0 Hz, 1H), 3.32 (s, 3H), 1.43-1.37 (m, 1H), 0.82-0.76 (m, 1H), 0.65-0.61 (m, 1H), 0.55-0.50 (m, 1H), 0.33-0.27 (m, 1H); LRMS (ESI) m/e 206.3 [(M+H)$^+$, calcd for $C_{10}H_{13}N_2O_2Cl_2$ 263.0].

Part H. 3-Methyl-5-nitropyridin-2-ol

A 3-necked, 2-L, round-bottomed flask equipped with a mechanical stirrer, an addition funnel and a thermometer was placed in an ice-water bath. Conc. $H_2SO_4$ (150 mL) was added to the flask. 2-Amino-3-methylpyridine (50.0 g, 0.463 mol, Lancaster, CAS 1603-40-3, mp. 29° C., prewarmed in a warm water bath to melt it) was weighed out in a 125 mL Erlenmeyer flask and was subsequently added in small portions via a prewarmed Pasteur pipet with the narrow tip broken off. The Erlenmeyer flask was kept in a warm water bath during the addition to prevent the starting material from solidifying. The temperature rose to ca. 45° C. during the addition and white smoke/fog formed within the flask. Conc. $H_2SO_4$ (100 mL) was added to the residual starting material and the mixture was added to the reaction flask. The resulting mixture was a milky-white suspension. A solution of conc. $H_2SO_4$ (35 mL) and 70% nitric acid (35 mL) was premixed with ice-water bath cooling and transferred into the addition funnel. After the internal temperature of the reaction mixture had cooled to 10-15° C. (but not below 10° C.), the premixed $H_2SO_4/HNO_3$ acid mixture was added dropwise at a rate such that the internal reaction temperature rose to 20-25° C. (5-10 min addition time). After the addition was complete, the ice-water bath was replaced with a tap-water bath. The reaction temperature slowly increased to ca. 30° C. range and then cooled down to room temperature. The reaction should be monitored during this time to ensure that the temperature does not rise too high. The reaction mixture was then stirred overnight and then 70% nitric acid (35 mL) was added dropwise via the addition funnel to the dark red-brown mixture at a rate of addition such that the temperature did not exceed 35° C. At this time, the reaction flask was sitting in a water bath containing water at room temperature. Water (500 mL) was then added to the reaction flask in portions via addition funnel. The first ca. 150 mL of water was added dropwise while allowing the internal temperature to climb slowly to 50-60° C. The rate of stirring was increased in order to break up any foaming that occurred. Brown gas evolved during the addition of the initial ca. 150 mL of water. The remaining ca. 350 mL of water was added at a faster rate after gas evolution had stopped and a temperature increase was no longer observed. The reaction turned from a dark cloudy brown to a clear orange solution. Some yellow precipitate may form as the reaction cools to below 50° C. The water bath was then removed, and replaced with a heating mantle, and the addition funnel was replaced with a condenser. The reaction mixture (a light orange solution or bright yellow solution) was then heated at 115-118° C. for 1.75-2 h. Additional gas evolution occurred at ca. 115° C. during this time. The reaction mixture was then cooled to room temperature with the aid of an ice-water bath and was then cooled further to 0° C. by adding ice directly into the reaction mixture. The solid that formed was collected on a Buchner funnel and was washed with cold water followed by a minimal amount of cold ethanol followed by a minimal amount of cold ether. The solid was then dried under vacuum to afford 3-methyl-5-nitropyridin-2-ol (53.5 g, 75% yield) as a pale yellow solid: mp 228-229° C.; $^1$H NMR (400 MHz, DMSO-$d_6$) δ 12.55 (s, br, 1H), 8.54 (d, J=3.0 Hz, 1H), 8.04 (d, J=2.0 Hz, 1H), 2.04 (s, 3H); $^{13}$C NMR (100 MHz, $CDCl_3$) δ 162.2, 135.4, 130.0, 129.5, 128.1, 15.8; LRMS, (ESI) m/e 152.96 [(M–H)$^-$, calcd for $C_6H_5N_2O_3$, 153.03].

Part I. 2-Methoxy-3-methyl-5-nitropyridine $POCl_3$ (410 ml) was added slowly, with stirring, to 3-methyl-5-nitropyridin-2-ol (75.0 g, 0.487 mol) [J. Org. Chem. 14, 328-32 (1949)] from Part H in a 4 neck, 3 L round bottom flask (temperature rose to 30° C.) and the reaction mixture was heated at 85° C. for 16 h. The solution was cooled and the excess $POCl_3$ was removed in vacuo. The residue was poured onto wet ice (4 L beaker) with stirring and the precipitate were collected by filtration and air dried, followed by drying in the vacuum oven to give 2-chloro-3-methyl-5-nitropyridine (75.0 g, 89% yield) as an off-white solid which was used in the next step without further purification: $^1$H NMR (300 MHz, $CDCl_3$) δ 9.04 (d, J=2.5 Hz, 1H), 8.33 (d, J=2.2 Hz, 1H), 2.50 (s, 3H).

2-Chloro-3-methyl-5-nitropyridine (67.0 g, 0.389 mol) was dissolved in anhydrous methanol (600 ml) and 0.5 M NaOMe in MeOH (800 mL) was added slowly to the mixture (temperature rises to ca. 30° C.). The reaction mixture was stirred at room temperature overnight. The solution was concentrated and the residue was transferred to a separatory funnel containing water (2 L). The aqueous layer was extracted with $CH_2Cl_2$ (2×2 L). The combined organic layers were dried over $MgSO_4$, filtered and concentrated to give 2-methoxy-3-methyl-5-nitropyridine (63.0 g, 97% yield) as a white solid which was dried under vacuum: $^1$H NMR (400 MHz, $CDCl_3$) δ 8.91 (d, J=2.0 Hz, 1H), 8.16 (s, 1H), 4.06 (s, 3H), 2.25 (s, 3H); $^{13}$C NMR (100 MHz, $CDCl_3$) δ 165.83, 141.91, 139.37, 132.92, 121.77, 54.83, 15.84; An analytical sample was recrystallized from hexane to give white needles, mp 95-96. 5° C.

Part J. 2-(Dibromomethyl)-6-methoxy-5-methyl-3-nitropyridine

To a 3 neck, 22 L round bottom flask equipped with a mechanical stirrer and an addition funnel was added potassium t-butoxide (450 g, 4.00 mol) and THF (4 L). The mixture was stirred vigorously and a solution of 2-methoxy-3-methyl-5-nitropyridine (100 g, 0.595 mol) from Part I and bromoform (195.4 g, 0.773 mol) in 500 mL of dry THF was added dropwise at such a rate that the temperature did not rise above –74° C. (3 h addition time). The reaction mixture was stirred at –78° C. for an additional 15 min. The reaction mixture was then quenched by the dropwise addition of a mixture of methanol (400 ml) and conc. HCl (600 mL) while maintaining the temperature below –68° C. Water (1 L) was then added and the aqueous layer was extracted with EtOAc (3×4 L). The combined organic layers were washed with brine, dried over MgSO$_4$, filtered and concentrated. The product was purified by column chromatography on silica gel (0%→7% ethyl acetate in hexanes) to give 2-(dibromomethyl)-6-methoxy-5-methyl-3-nitropyridine (190.0 g, 94% yield) as a red-brown solid: mp 58.7-61.2° C. $^1$H NMR (300 mHz, CDCl$_3$) δ 8.04 (s, 1H), 7.60 (s, 1H), 4.15 (s, 3H), 2.26 (s, 1H); LRMS, (ESI) m/e 339.0 [(M+H)$^+$, calcd for C$_8$H$_9$N$_2$O$_3$Br$_2$, 338.9].

Part K. 6-Methoxy-2,5-dimethylpyridin-3-amine

To a solution of 2-(dibromomethyl)-6-methoxy-5-methyl-3-nitropyridine (110 g, 0.323 mol) from Part J, in EtOH (1.1 L) in a Parr bottle was added triethylamine (135 mL, 0.970 mol) followed by 10% Pd/C (11.0 g). The mixture placed on a Parr shaker under an H$_2$ atm at 45 psi for 18 h. The reaction mixture was filtered through Celite and the filtrate was concentrated. The residue was partitioned between water and EtOAc and the organic layer was washed with water, brine, dried over MgSO$_4$, filtered and concentrated. The residue was purified by column chromatography on silica gel (10%→20%→35%→50% ethyl acetate in hexanes) to give 6-methoxy-2,5-dimethylpyridin-3-amine (35.7 g, 73% yield) as a light-brown solid: mp 39.8-41° C.; $^1$H NMR (400 mHz, DMSO-d$_6$) δ 6.82 (s, 1H), 4.37 (s, 2H), 3.73 (s, 3H), 2.16 (s, 3H), 2.00 (s, 3H); $^{13}$C NMR (100 mHz, DMSO-d$_6$) δ 152.7, 135.8, 134.8, 126.3, 116.1, 52.1, 19.2, 14.7; LRMS, (ESI) m/e 153.2 [(M+H)$^+$, calcd for C$_8$H$_{13}$N$_2$O, 153.1].

Part L. (S)-5-Chloro-1-(1-cyclopropyl-2-methoxyethyl)-3-(6-methoxy-2,5-dimethylpyridin-3-ylamino) pyrazin-2(1H)-one To a solution of (S)-3,5-dichloro-1-(1-cyclopropyl-2-methoxyethyl)pyrazin-2(1H)-one (4.00 g, 15.2 mmol) from Part G and 6-methoxy-2,5-dimethylpyridin-3-amine (2.31 g, 15.2 mmol) from Part K in THF (76 mL) at 0° C. was added NaHMDS (31.9 mL, 31.9 mmol, 1 M in THF). The reaction mixture was stirred at room temperature for 1 h. The mixture was transferred to a separatory funnel containing saturated aqueous NaHCO$_3$ solution. The aqueous layer was extracted with EtOAc (3×100 mL). The combined organic layers were washed with brine, dried over MgSO$_4$, filtered and concentrated. The residue was purified by column chromatography on silica gel (10% 40% ethyl acetate in hexanes) to afford (S)-5-chloro-1-(1-cyclopropyl-2-methoxyethyl)-3-(6-methoxy-2,5-dimethylpyridin-3-ylamino)pyrazin-2(1H)-one (4.94 g, 86% yield) as a light-brown amorphous solid. Recrystallization from hexanes/ethyl acetate (1:1, 10 mL) to afforded a light-brown crystalline solid: mp 99-100.5° C.; $[\alpha]^{25}_D$ −52.3 (c 0.636, CHCl$_3$); $^1$H NMR (400 MHz, CDCl$_3$) δ 8.05 (s, 1H), 7.88 (s, 1H), 6.90 (s, 1H), 4.19-4.14 (m, 1H), 3.92 (s, 3H), 3.74 (dd, J$_{AB}$10.3, J$_{AX}$=6.2 Hz, 1H), 3.67 (dd, J$_{BA}$=10.3, J$_{BX}$=3.5 Hz, 1H), 3.34 (s, 3H), 2.41 (s, 3H), 2.17 (s, 3H), 1.31-1.24 (m, 1H), 0.80-0.73 (m, 1H), 0.62-0.56 (m, 1H), 0.53-0.47 (m, 1H), 0.36-0.30 (m, 1H); HRMS (ESI) m/e 379.1537 [(M+H)$^+$, calcd for C$_{18}$H$_{24}$N$_4$O$_3$Cl 379.1537].

Part M. (S)-5-Chloro-1-(cyclopropyl-2-hydroxyethyl)-3-(6-methoxy-2,5-dimethylpyridin-3-ylamino) pyrazin-2(1H)-one A solution of (S)-5-chloro-1-(cyclopropyl-2-methoxyethyl)-3-(6-methoxy-2,5-dimethylpyridin-3-ylamino) pyrazin-2(1H)-one (1.72 g, 4.39 mmol) from Part L in CH$_2$Cl$_2$ (50 mL) at −78° C. was treated with BBr$_3$ (9.65 mL, 9.65 mmol, 1 M in CH$_2$Cl$_2$) dropwise via syringe. After the addition was complete, the reaction mixture was allowed to warm to −40° C., and was stirred at −40 to −35° C. for 45 min. The reaction was quenched by the addition of saturated aqueous NaHCO$_3$. The mixture was then transferred to a separatory funnel containing saturated aqueous NaHCO$_3$ (50 L). The aqueous layer was extracted with EtOAc (3×50 mL). The combined organic layers were washed with brine, dried over MgSO$_4$, filtered, and concentrated. The product was purified by column chromatography on silica gel (30%→55% ethyl acetate in hexanes) to afford (S)-5-chloro-1-(cyclopropyl-2-hydroxyethyl)-3-(6-methoxy-2,5-dimethylpyridin-3-ylamino)pyrazin-2(1H)-one (1.50 g, 94% yield) as a light yellow amorphous solid: $^1$H NMR (400 MHz, CDCl$_3$) δ 8.03 (s, 1H), 7.87 (s, 1H), 6.89 (s, 1H), 4.07-4.00 (m, 3H), 3.95 (d, J=6.8 Hz, 1H), 3.94 (s, 3H), 2.42 (s, 3H), 2.17 (s, 3H), 1.27-1.23 (m, 1H), 0.83-0.79 (m, 1H), 0.66-0.62 (m, 1H), 0.55-0.51 (m, 1H), 0.35-0.32 (m, 1H); LRMS (ESI) m/e 365.08 [(M+H)$^+$, calcd for C$_{17}$H$_{22}$N$_4$O$_3$Cl 365.14].

Part N. (S)-2-(5-Chloro-3-(6-methoxy-2,5-dimethylpyridin-3-ylamino)-2-oxopyrazin-1(2H)-yl)-2-cyclopropylethyl phenylcarbamate A solution of (S)-5-chloro-1-(cyclopropyl-2-hydroxyethyl)-3-(6-methoxy-2,5-dimethylpyridin-3-ylamino) pyrazin-2(1H)-one (20 mg, 0.055 mmol) from Part M in THF (1 mL) at 0° C. was treated with NaH (7 mg, 0.275 mmol, prewashed with hexanes). The cooling bath was removed and the mixture was allowed to warm to room temperature and was stirred at room temperature for 30 min. The reaction mixture was cooled to 0° C. and a solution of phenyl isocyanate (9 μL, 0.083 mmol) in 0.5 mL THF was added via cannula. The cooling bath was removed and the reaction mixture was allowed to warm to room temperature and was stirred at room temperature for 20 min. The reaction mixture was then cooled to 0° C. and was quenched by the addition of saturated aqueous NaHCO$_3$. The mixture was transferred to a separatory funnel containing saturated aqueous NaHCO$_3$ (5 mL) and the aqueous layer was extracted with EtOAc (3×10 mL). The combined organic layers were washed with brine, dried over MgSO$_4$, filtered, and concentrated. The product was purified by column chromatography on silica gel (20% 30% ethyl acetate in hexanes) to furnish (S)-2-(5-chloro-3-(6-methoxy-2,5-dimethylpyridin-3-ylamino)-2-oxopyrazin-1(2H)-yl)-2-cyclopropylethyl phenylcarbamate (14 mg, 52% yield) as a colorless amorphous solid: $^1$H NMR (400 MHz, CDCl$_3$) δ 8.15 (s, 1H), 7.92 (s, 1H), 7.30-7.26 (m, 4H), 7.06 (t, J=8.3 Hz, 1H), 6.82 (s, 1H), 6.63 (s br, 1H), 4.58 (dd, J$_{AB}$=11.9, J$_{AX}$=4.1 Hz, 1H), 4.48 (dd, J$_{BA}$=11.9, J$_{BX}$=7.6 Hz, 1H), 4.26-4.21 (m, 1H), 4.05 (s, 3H), 2.51 (s, 3H), 2.19 (s, 3H), 1.26-1.21 (m, 1H), 0.88-0.80 (m, 1H), 0.67-0.57 (m, 2H), 0.40-0.36 (m, 1H); HRMS (ESI) m/e 484.1753 [(M+H)$^+$, calcd for C$_{24}$H$_{27}$N$_5$O$_4$Cl 484.1752].

Example 2

(S)-2-(5-Chloro-3-(6-methoxy-2,5-dimethylpyridin-3-ylamino)-2-oxopyrazin-1(2H)-yl)-2-cyclopropyl-ethyl 3-cyanophenylcarbamate

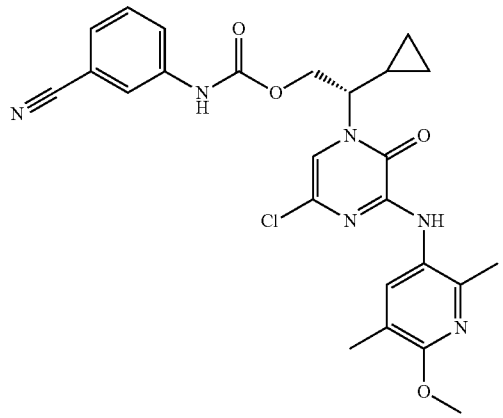 [SMILES: COc1nc(C)c(Nc2nc(Cl)cn([C@H](COC(=O)Nc3cccc(C#N)c3)C3CC3)c2=O)cc1C]

Prepared by the method described in Example 1 using the appropriate starting materials to give the desired product as a colorless solid: mp 206.5-207.2° C.; $^1$H NMR (400 MHz, CDCl$_3$) δ 8.02 (s, 1H), 7.90 (s, 1H), 7.75 (s, 1H), 7.53-7.50 (m, 1H), 7.40-7.32 (m, 2H), 6.87 (s, 1H), 6.79 (s, 1H), 4.61 (dd, $J_{AB}$=11.8, $J_{AX}$=4.0 Hz, 1H), 4.48 (dd, $J_{BA}$=11.8, $J_{BX}$=8.1 Hz, 1H), 4.28-4.24 (m, 1H), 3.93 (s, 3H), 2.41 (s, 3H), 2.17 (s, 3H), 1.26-1.20 (m, 1H), 0.87-0.83 (m, 1H), 0.69-0.58 (m, 2H), 0.41-0.37 (m, 1H); HRMS (ESI) m/e 509.1723 [(M+H)$^+$, calcd for C$_{25}$H$_{26}$N$_6$O$_4$Cl 509.1704].

Example 3

(S)-2-(5-Chloro-3-(6-methoxy-2,5-dimethylpyridin-3-ylamino)-2-oxopyrazin-1(2H)-yl)-2-cyclopropyl-ethyl pyridin-3-ylcarbamate

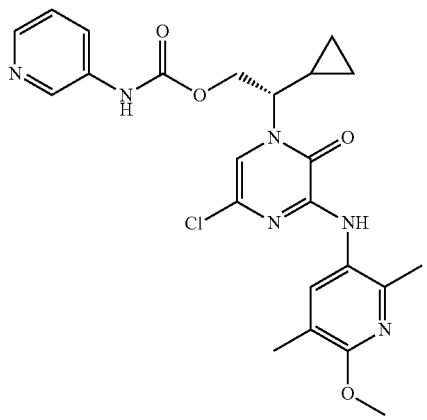 [SMILES: COc1nc(C)c(Nc2nc(Cl)cn([C@H](COC(=O)Nc3cccnc3)C3CC3)c2=O)cc1C]

Prepared by the method described in Example 1 using the appropriate starting materials to give the desired product as a colorless amorphous solid: $^1$H NMR (400 MHz, CDCl$_3$) δ 8.50 (s, 1H), 8.28 (d, J=3.7 Hz, 1H), 7.98 (s, 2H), 7.89 (s, 1H), 7.45 (s br, 1H), 7.28-7.24 (m, 1H), 6.81 (s, 1H), 4.59 (dd, $J_{AB}$=11.8, $J_{AX}$3.7 Hz, 1H), 4.49 (dd, $J_{BA}$=11.8, $J_{BX}$7.8 Hz, 1H), 4.49-4.46 (m, 1H), 3.91 (s, 3H), 2.38 (s, 3H), 2.15 (s, 3H), 1.26-1.22 (m, 1H), 0.86-0.80 (m, 1H), 0.67-0.55 (m, 2H), 0.41-0.35 (m, 1H); HRMS (ESI) m/e 485.1720 [(M+H)$^+$, calcd for C$_{23}$H$_{26}$N$_6$O$_4$Cl 485.1704].

Example 4

(S)-2-(5-Chloro-3-(6-methoxy-2,5-dimethylpyridin-3-ylamino)-2-oxopyrazin-1(2H)-yl)-2-cyclopropyl-ethyl 2-chlorophenylcarbamate

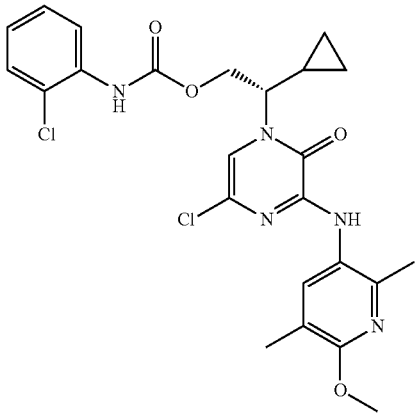 [SMILES: COc1nc(C)c(Nc2nc(Cl)cn([C@H](COC(=O)Nc3ccccc3Cl)C3CC3)c2=O)cc1C]

Prepared by the method described in Example 1 using the appropriate starting materials to give the desired product as a yellow amorphous solid: $^1$H NMR (400 MHz, CDCl$_3$) δ 8.02 (s, 2H), 7.90 (s, 1H), 7.32 (dd, J=8.0, 1.5 Hz, 1H), 7.24 (dt, J=7.3, 1.2 Hz, 1H), 7.07 (s br, 1H), 6.99 (dt, J=7.8, 1.5 Hz, 1H), 6.80 (s, 1H), 4.63 (dd, $J_{AB}$=11.6, $J_{AX}$=4.0 Hz, 1H), 4.49 (dd, $J_{BA}$=11.6, $J_{BX}$=7.3 Hz, 1H), 4.27-4.22 (m, 1H), 3.92 (s, 3H), 2.40 (s, 3H), 2.17 (s, 3H), 1.29-1.22 (m, 1H), 0.88-0.82 (m, 1H), 0.68-0.58 (m, 2H), 0.40-0.37 (m, 1H); HRMS (ESI) m/e 518.1385 [(M+H)$^+$, calcd for C$_{24}$H$_{26}$N$_5$O$_4$Cl$_2$ 518.1362].

Example 5

(S)-2-(5-Chloro-3-(6-methoxy-2,5-dimethylpyridin-3-ylamino)-2-oxopyrazin-1(2H)-yl)-2-cyclopropyl-ethyl 4-chlorophenylcarbamate

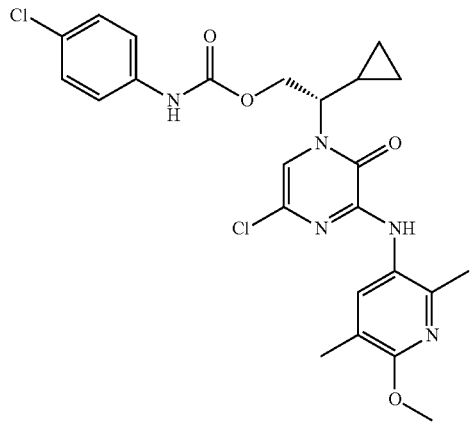 [SMILES: COc1nc(C)c(Nc2nc(Cl)cn([C@H](COC(=O)Nc3ccc(Cl)cc3)C3CC3)c2=O)cc1C]

Prepared by the method described in Example 1 using the appropriate starting materials to give the desired product as a yellow amorphous solid: $^1$H NMR (400 MHz, CDCl$_3$) δ 7.99 (s, 1H), 7.89 (s, 1H), 7.29-7.22 (m, 4H), 6.78 (s, 1H), 6.70 (s, 1H), 4.57 (dd, $J_{AB}$=11.8, $J_{AX}$=4.0 Hz, 1H), 4.46 (dd, $J_{BA}$11.8, $J_{BX}$7.8 Hz, 1H), 4.26-4.22 (m, 1H), 3.91 (s, 3H), 2.39 (s, 3H), 2.16 (s, 3H), 1.26-1.20 (m, 1H), 0.88-0.81 (m, 1H), 0.67-0.56 (m, 2H), 0.40-0.36 (m, 1-1); HRMS (ESI) m/e 518.1364 [(M+H)$^+$, calcd for C$_{24}$H$_{26}$N$_5$O$_4$Cl$_2$ 518.1362].

Example 6

(S)-2-(5-Chloro-3-(6-methoxy-2,5-dimethylpyridin-3-ylamino)-2-oxopyrazin-1(2H)-yl)-2-cyclopropyl-ethyl 3,5-dichlorophenylcarbamate

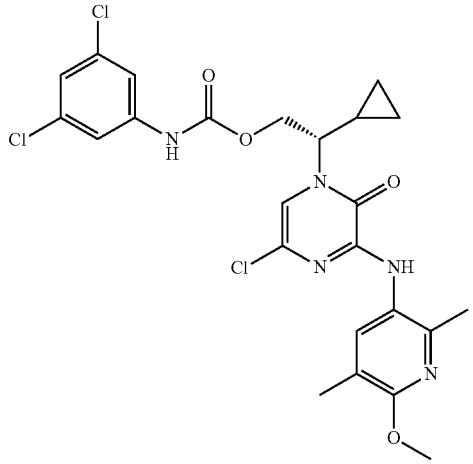 [SMILES: COc1nc(C)c(Nc2nc(Cl)cn([C@H](COC(=O)Nc3cc(Cl)cc(Cl)c3)C3CC3)c2=O)cc1C]

Prepared by the method described in Example 1 using the appropriate starting materials to give the desired product as a red amorphous solid: $^1$H NMR (400 MHz, CDCl$_3$) δ 7.93 (s, 1H), 7.89 (s, 1H), 7.29-7.21 (m, 3H), 7.01 (s, 1H), 6.74 (s, 1H), 4.59 (dd, $J_{AB}$=11.6, $J_{AX}$=3.6 Hz, 1H), 4.38 (dd, $J_{BA}$=11.6, $J_{BX}$=8.0 Hz, 1H), 4.27-4.21 (m, 1H), 3.90 (s, 3H), 2.36 (s, 3H), 2.13 (s, 3H), 1.20-1.14 (m, 1H), 0.88-0.82 (m, 1H), 0.64-0.56 (m, 2H), 0.39-0.36 (m, 1H); HRMS (ESI) m/e 552.0981 [(M+H)$^+$, calcd for C$_{24}$H$_{25}$N$_5$O$_4$Cl$_3$ 552.0972].

Example 7

(S)-2-(5-Chloro-3-(6-methoxy-2,5-dimethylpyridin-3-ylamino)-2-oxopyrazin-1(2H)-yl)-2-cyclopropyl-ethyl 2,4-dichlorophenylcarbamate

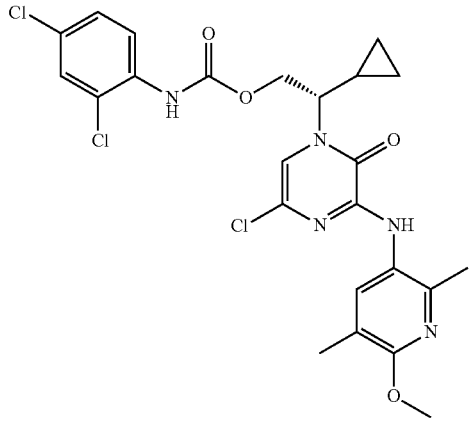 [SMILES: COc1nc(C)c(Nc2nc(Cl)cn([C@H](COC(=O)Nc3ccc(Cl)cc3Cl)C3CC3)c2=O)cc1C]

Prepared by the method described in Example 1 using the appropriate starting materials to give the desired product as a yellow amorphous solid: $^1$H NMR (400 MHz, CDCl$_3$) δ 8.01 (s, 2H), 7.90 (s, 1H), 7.34 (d, J=2.6 Hz, 1H), 7.22 (dd, J=8.8, 2.2 Hz, 1H), 7.01 (s br, 1H), 6.79 (s, 1H), 4.63 (dd, $J_{AB}$=11.8, $J_{AX}$=4.0 Hz, 1H), 4.47 (dd, $J_{BA}$=11.8, $J_{BX}$=7.5 Hz, 1H), 4.27-4.21 (m, 1H), 3.92 (s, 3H), 2.40 (s, 3H), 2.17 (s, 3H), 1.27-1.21 (m, 1H), 0.88-0.81 (m, 1H), 0.68-0.57 (m, 2H), 0.41-0.37 (m, 1H); HRMS (ESI) m/e 552.0981 [(M+H)$^+$, calcd for C$_{24}$H$_{25}$N$_5$O$_4$Cl$_3$ 552.0972].

Example 8

(S)-2-(5-Chloro-3-(6-methoxy-2,5-dimethylpyridin-3-ylamino)-2-oxopyrazin-1(2H)-yl)-2-cyclopropyl-ethyl butylcarbamate

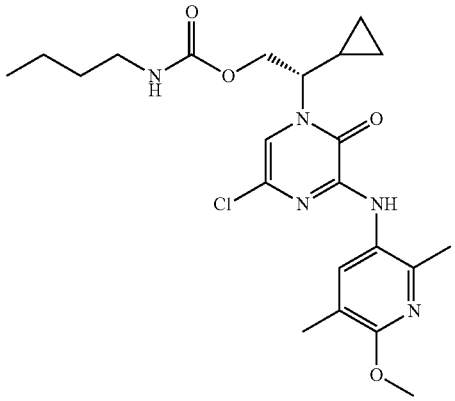 [SMILES: CCCCNC(=O)OC[C@H](C1CC1)n1cc(Cl)nc(Nc2cc(C)c(OC)nc2C)c1=O]

Prepared by the method described in Example 1 using the appropriate starting materials to give the desired product as a red amorphous solid: $^1$H NMR (400 MHz, CDCl$_3$) δ 8.05 (s, 1H), 7.90 (s, 1H), 6.76 (s, 1H), 4.67-4.63 (m, 1H), 4.47 (dd, $J_{AB}$=11.8, $J_{AX}$=4.0 Hz, 1H), 4.35 (dd, $J_{BA}$=11.8, $J_{BX}$=7.6 Hz, 1H), 4.19-4.15 (m, 1H), 3.92 (s, 3H), 3.16-3.11 (m, 2H), 2.41 (s, 3H), 2.17 (s, 3H), 1.48-1.41 (m, 2H), 1.35-1.19 (m, 3H), 0.89 (t, J=7.3 Hz, 3H), 0.84-0.78 (m, 1H), 0.63-0.54 (m, 2H), 0.37-0.33 (m, 1H); HRMS (ESI) m/e 464.2081 [(M+H)$^+$, calcd for C$_{22}$H$_{31}$N$_5$O$_4$Cl 464.2065].

Example 9

(S)-2-(5-Chloro-3-(6-methoxy-2,5-dimethylpyridin-3-ylamino)-2-oxopyrazin-1(2H)-yl)-2-cyclopropyl-ethyl propylcarbamate

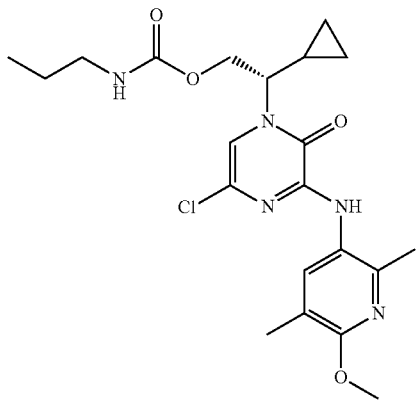 [SMILES: CCCNC(=O)OC[C@H](C1CC1)n1cc(Cl)nc(Nc2cc(C)c(OC)nc2C)c1=O]

Prepared by the method described in Example 1 using the appropriate starting materials to give the desired product as a yellow amorphous solid: $^1$H NMR (400 MHz, CDCl$_3$) δ 8.03 (s, 1H), 7.90 (s, 1H), 6.76 (s, 1H), 4.72 (s br, 1H), 4.46 (dd, $J_{AB}$=11.8, $J_{AX}$=3.7 Hz, 1H), 4.35 (dd, $J_{BA}$=11.8, $J_{BX}$=7.6 Hz, 1H), 4.19-4.14 (m, 1H), 3.91 (s, 3H), 3.22-3.17 (m, 2H), 2.40 (s, 3H), 2.16 (s, 3H), 1.57-1.47 (m, 2H), 1.23-1.19 (m, 1H), 0.87 (t, J=7.1 Hz, 3H), 0.84-0.77 (m, 1H), 0.62-0.52 (m, 2H), 0.36-0.32 (m, 1H); HRMS (ESI) m/e 450.1912 [(M+H)$^+$, calcd for $C_{21}H_{29}N_5O_4Cl$ 450.1908].

Example 10

(S)-2-(5-Chloro-3-(6-methoxy-2,5-dimethylpyridin-3-ylamino)-2-oxopyrazin-1(2H)-yl)-2-cyclopropylethyl ethylcarbamate

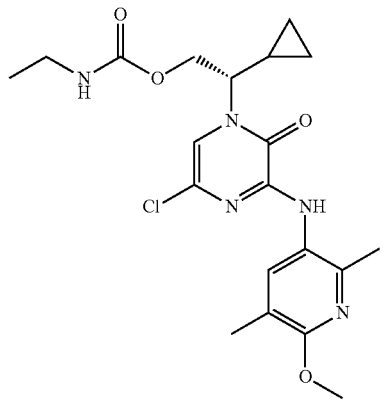 [SMILES: CCNC(=O)OC[C@H](C1CC1)n1cc(Cl)nc(Nc2cc(C)c(OC)nc2C)c1=O]

Prepared by the method described in Example 1 using the appropriate starting materials to give the desired product as a yellow amorphous solid: $^1$H NMR (400 MHz, CDCl$_3$) δ 8.04 (s, 1H), 7.90 (s, 1H), 6.77 (s, 1H), 4.67 (s br, 1H), 4.47 (dd, $J_{AB}$=11.6, $J_{AX}$=3.7 Hz, 1H), 4.35 (dd, $J_{BA}$=11.6, $J_{BX}$=7.5 Hz, 1H), 4.19-4.15 (m, 1H), 3.91 (s, 3H), 3.21-3.14 (m, 2H), 2.41 (s, 3H), 2.17 (s, 3H), 1.26-1.19 (m, 1H), 1.10 (t, J=7.3 Hz, 3H), 0.83-0.78 (m, 1H), 0.63-0.52 (m, 2H), 0.38-0.33 (m, 1H); HRMS (ESI) m/e 436.1760 [(M+H)$^+$, calcd for $C_{20}H_{27}N_5O_4Cl$ 436.1752].

Example 11

(S)-2-(5-Chloro-3-(6-methoxy-2,5-dimethylpyridin-3-ylamino)-2-oxopyrazin-1(2H)-yl)-2-cyclopropylethyl 6-ethoxy-2,5-dimethylpyridin-3-ylcarbamate

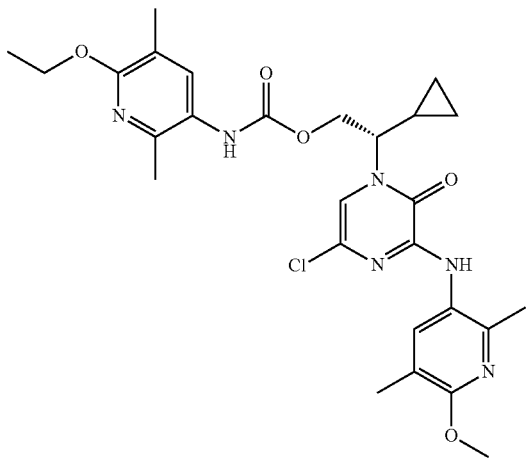 [SMILES: CCOc1nc(C)c(NC(=O)OC[C@H](C2CC2)n2cc(Cl)nc(Nc3cc(C)c(OC)nc3C)c2=O)cc1C]

Part A. (S)-2-(5-Chloro-3-(6-methoxy-2,5-dimethylpyridin-3-ylamino)-2-oxopyrazin-1(2H)-yl)-2-cyclopropylethyl 4-nitrophenyl carbonate To a solution of (S)-5-chloro-1-(cyclopropyl-2-hydroxyethyl)-3-(6-methoxy-2,5-dimethylpyridin-3-ylamino)pyrazin-2(1H)-one (250 mg, 0.68 mmol) from Example 1 Part M, in CH$_2$Cl$_2$ (15 mL) at 0° C. was added triethylamine (284 µL, 2.04 mmol) followed by 4-nitrophenylchloroformate (250 mg, 1.23 mmol) in CH$_2$Cl$_2$ via cannula. The cooling bath was removed and the reaction mixture was stirred at room temperature for 4 h. The reaction mixture was concentrated and the residue was purified by column chromatography on silica gel (20%→30% ethyl acetate in hexanes) to afford (S)-2-(5-chloro-3-(6-methoxy-2,5-dimethylpyridin-3-ylamino)-2-oxopyrazin-1(2H)-yl)-2-cyclopropylethyl 4-nitrophenyl carbonate (180 mg, 50% yield) as a yellow amorphous solid: $^1$H NMR (400 MHz, CDCl$_3$) δ 8.25 (d, J=9.1 Hz, 2H), 7.98 (s, 1H), 7.90 (s, 1H), 7.35 (d, J=9.1 Hz, 2H), 6.85 (s, 1H), 4.70 (dd, $J_{AB}$=11.6, $J_{AX}$=3.6 Hz, 1H), 4.51 (dd, $J_{BA}$ 11.6, $J_{BX}$=7.0 Hz, 1H), 4.30-4.25 (m, 1H), 3.91 (s, 3H), 2.38 (s, 3H), 2.16 (s, 3H), 1.31-1.25 (m, 1H), 0.91-0.84 (m, 1H), 0.75-0.68 (m, 1H), 0.63-0.57 (m, 1H), 0.43-0.38 (m, 1H); LRMS (ESI) m/e 530.02 [(M+H)$^+$, calcd for $C_{24}H_{24}N_5O_7Cl$ 530.14].

Part B. (S)-2-(5-Chloro-3-(6-methoxy-2,5-dimethylpyridin-3-ylamino)-2-oxopyrazin-1(2H)-yl)-2-cyclopropylethyl 6-ethoxy-2,5-dimethylpyridin-3-ylcarbamate To a solution of (S)-2-(5-chloro-3-(6-methoxy-2,5-dimethylpyridin-3-ylamino)-2-oxopyrazin-1(2H)-yl)-2-cyclopropylethyl 4-nitrophenyl carbonate (30 mg, 0.057 mmol) from Part A, 6-ethoxy-2,5-dimethylpyridin-3-amine (17 mg, 0.100 mmol), HOBt (9 mg, 0.063 mmol) and 4 Å molecular sieves (60 mg) in THF (1 mL) at room temperature was added triethylamine (23 µL, 0.17 mmol). The reaction mixture was stirred at room temperature for 48 h. The mixture was transferred to a separatory funnel containing 1 N HCl (5 mL) and the aqueous layer was extracted with EtOAc (3×10 ml). The combined organic layers were washed with brine, dried over MgSO$_4$, filtered, and concentrated. The residue was purified by HPLC (MeCN/H$_2$O with 0.1% TFA, C$_{18}$ column) to afford (S)-2-(5-chloro-3-(6-methoxy-2,5-dimethylpyridin-3-ylamino)-2-oxopyrazin-1(2H)-yl)-2-cyclopropylethyl 6-ethoxy-2,5-dimethylpyridin-3-ylcarbamate (10 mg, 32% yield) as a yellow amorphous solid: $^1$H NMR (400 MHz, CDCl$_3$) δ 8.05 (s, 1H), 7.92 (s, 1H), 7.44 (s, 1H), 6.80 (s, 1H), 6.13 (s, 1H), 4.61-4.58 (m, 1H), 4.43 (dd, $J_{AB}$=11.6, $J_{AX}$=7.5 Hz, 1H), 4.31 (q, J=6.8 Hz, 2H), 4.26-4.21 (m, 1H), 3.92 (s, 3H), 2.41 (s, 3H), 2.29 (s, 3H), 2.17 (s, 3H), 2.10 (s, 3H), 1.33 (t, J=7.0 Hz, 3H), 1.25-1.19 (m, 1H), 0.88-0.81 (m, 1H), 0.65-0.55 (m, 2H), 0.38-0.34 (m, 1H); HRMS (ESI) m/e 557.2269 [(M+H)$^+$, calcd for $C_{27}H_{34}N_6O_5Cl$ 557.2279].

Example 12

(S)-2-(5-Chloro-3-(6-methoxy-2,5-dimethylpyridin-3-ylamino)-2-oxopyrazin-1(2H)-yl)-2-cyclopropyl ethyl 6-methoxy-2,5-dimethylpyridin-3-ylcarbamate

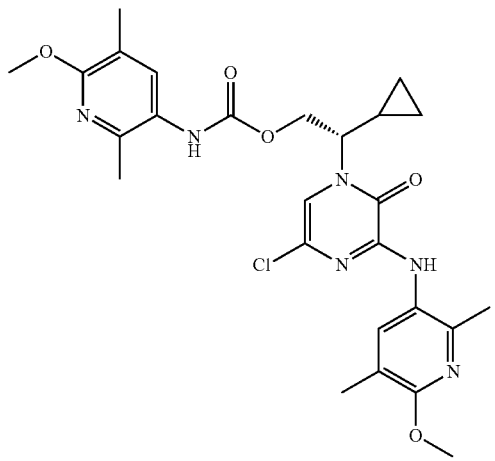

Prepared by the method described in Example 11 using the appropriate starting materials to give the desired product as a yellow amorphous solid: $^1$H NMR (400 MHz, CDCl$_3$) δ 8.05 (s, 1H), 7.91 (s, 1H), 7.46 (s, 1H), 6.80 (s, 1H), 6.13 (s, 1H), 4.61-4.57 (m, 1H), 4.44 (dd, J$_{AB}$=11.6, J$_{AX}$=7.9 Hz, 1H), 4.25-4.19 (m, 1H), 3.92 (s, 3H), 3.88 (s, 3H), 2.41 (s, 3H), 2.31 (s, 3H), 2.17 (s, 3H), 2.10 (s, 3H), 1.24-1.20 (m, 1H), 0.88-0.82 (m, 1H), 0.65-0.56 (m, 2H), 0.38-0.34 (m, 1H); HRMS (ESI) m/e 543.2113 [(M+H)$^+$, calcd for C$_{26}$H$_{32}$N$_6$O$_5$Cl 543.2123].

Example 13

(S)-2-(5-Chloro-3-(6-methoxy-2,5-dimethylpyridin-3-ylamino)-2-oxopyrazin-1(2H)-yl)-2-cyclopropylethyl 6-methoxy-2-dimethylpyridin-3-ylcarbamate

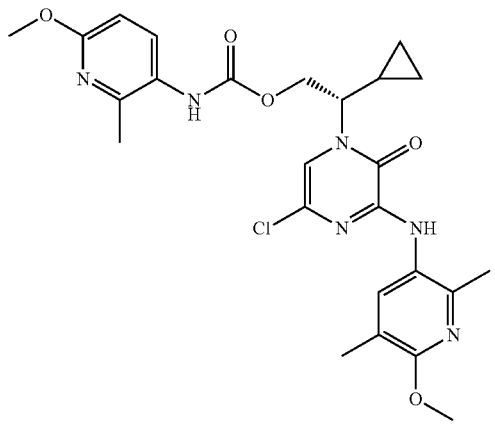

Prepared by the method described in Example 11 using the appropriate starting materials to give the desired product as a yellow amorphous solid: $^1$H NMR (400 MHz, CDCl$_3$ δ 8.04 (s, 1H), 7.90 (s, 1H), 7.67 (s, 1H), 6.81-6.79 (m, 1H), 6.55 (d, J=8.5 Hz, 1H), 6.16 (s, 1H), 4.63-4.57 (m, 1H), 4.43 (dd, J$_{AB}$=10.5, J$_{AX}$=7.5 Hz, 1H), 4.26-4.21 (m, 1H), 3.92 (s, 3H), 3.86 (s, 3H), 2.41 (s, 3H), 2.35 (s, 3H), 2.18 (s, 3H), 1.27-1.21 (m, 1H), 0.88-0.82 (m, 1H), 0.67-0.55 (m, 2H), 0.39-0.34 (m, 1H); HRMS (ESI) m/e 529.1974 [(M+H)$^+$, calcd for C$_{25}$H$_{30}$N$_6$O$_5$Cl 529.1966].

Example 14

(S)-2-(5-Chloro-3-(6-(difluoromethoxy)-2,5-dimethylpyridin-3-ylamino)-2-oxopyrazin-1(2H)-yl)-2-cyclopropylethyl phenylcarbamate

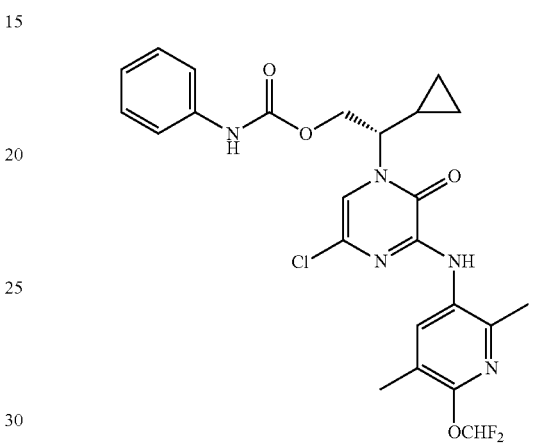

Part A. tert-Butyl 2-(6-methoxy-5-methyl-3-nitropyridin-2-yl)acetate

A yellow solution of 2-methoxy-3-methyl-5-nitropyridine (68.8 g, 409 mmol) from Example 1 Part I and tert-butyl 2-chloroacetate (77.0 g, 511 mmol) in THF (1 L) was stirred and cooled to −20° C. in a dry ice/isopropanol bath. Potassium tert-butoxide (115 g, 1.02 mol) was added at a rate so that the reaction temperature was less than −10° C. The reaction mixture turned dark purple. When the addition was complete, the cooling bath was removed and the reaction was stirred for 30 min. The stirred reaction mixture was quenched with HCl (500 mL, 2.4 N). The purple solution turned pale yellow and the mixture separated into two layers. The organic layer was separated, washed three times with brine, and concentrated in vacuo. Hexane was added to the amber residue. The mixture was concentrated in vacuo and then dried under high vacuum for 1 hr to give tert-butyl 2-(6-methoxy-5-methyl-3-nitropyridin-2-yl)acetate (83.4 g, 72% yield) as a tan solid: $^1$H NMR (400 MHz, CDCl$_3$) δ 8.16 (s, 1H), 4.09 (s, 2H), 4.02 (s, 2H), 2.21 (s, 3H), 1.44 (s, 9H); $^{13}$C NMR (100 MHz, CDCl$_3$) δ 168.81, 163.63, 147.88, 139.41, 135.19, 120.82, 81.66, 54.69, 44.48, 28.03, 15.27. An analytical sample was recrystallized from hexane to give white needles, mp 71-72.5° C.

Part B.
2-(6-Methoxy-5-methyl-3-nitropyridin-2-yl)acetic acid

A solution of tert-butyl 2-(6-methoxy-5-methyl-3-nitropyridin-2-yl)acetate (83.0 g, 294 mmol) from Part A in TFA (200 mL) was heated in a hot water bath for 1 h. The solution was concentrated in vacuo to give a brown oil. The oil was diluted with hexane and stirred. The resulting solid was collected by filtration and air dried to give 2-(6-methoxy-5-methyl-3-nitropyridin-2-yl)acetic acid (62.8 g, 94% yield) as a tan solid: $^1$H NMR (400 MHz, CDCl$_3$) δ 8.70 (s br, 1H), 8.20 (s, 1H), 4.25 (s, 2H), 4.03 (s, 3H), 2.24 (s, 3H); $^{13}$C NMR (100 MHz, CDCl$_3$) δ 175.59, 163.80, 146.52, 139.16, 135.30, 121.53, 54.86, 42.88, 15.32. An analytical sample was recrystallized from hexane: mp 135-137° C.

Part C. 2-Methoxy-3,6-dimethyl-5-nitropyridine

A mixture of tert-butyl 2-(6-methoxy-5-methyl-3-nitropyridin-2-yl)acetate (62.5 g, 276 mmol) from Part B, K$_2$CO$_3$ (20.0 g, 145 mmol), and DMF (100 mL) was heated with stirring in a hot water bath to 90° C. for 1 h. Gas evolution was noted during the heating period and had ceased after 1 hour. The mixture was poured into stirred ice water (600 mL), with washing of the reaction flask with a small volume of acetone. The resulting precipitate was collected by filtration and air dried to give 2-methoxy-3,6-dimethyl-5-nitropyridine (48.5 g, 96% yield) as a tan solid: $^1$H NMR (400 MHz, CDCl$_3$) δ 8.08 (s, 1H), 4.02 (s, 3H), 2.76 (d, 3H), 2.19 (s, 3H); $^{13}$C NMR (100 MHz, CDCl$_3$) δ 163.37, 151.63, 139.44, 135.02, 119.39, 54.45, 24.18, 15.16. An analytical sample was recrystallized from hexanes to give tan needles: mp 85.9-90.5° C.

Part D. 2-Methoxy-3,6-dimethyl-5-nitropyridine

Alternate Procedure to the Three Step Procedure Described in Parts A, B, and C Above.

Dimethyl sulfoxide (35 mL) was added to a dry round-bottomed flask containing NaH (1.82 g, 45.5 mmol, 60% in mineral oil). The resulting suspension was heated at 70° C. for 35 min during which time the suspension became a solution. The reaction mixture was cooled to room temperature, trimethylsulfoxonium iodide (10.0 g, 45.5 mmol) was added, and the mixture was stirred at room temperature for 30 min. 2-Methoxy-3-methyl-5-nitropyridine (4.50 g, 26.80 mmol) from Example 1 Part I, was added and the resulting dark red solution was stirred at room temperature for 30 min, at which time TLC showed complete consumption of starting material. The reaction mixture was transferred to a separatory funnel containing water (30 mL), and the aqueous layer was extracted with EtOAc (3×100 mL). The combined organic layers were washed with brine, dried over MgSO$_4$, filtered and concentrated. The residue was purified by column chromatography on silica gel (20% ethyl acetate in hexanes) to afford 2-methoxy-3,6-dimethyl-5-nitropyridine (2.00 g, 41% yield) as a colorless solid: mp 85.5-86.2° C.; $^1$H NMR (400 MHz, CDCl$_3$) δ 8.08 (s, 1H), 4.02 (s, 3H), 2.77 (s, 3H), 2.20 (s, 3H).

Part E. 3,6-Dimethyl-5-nitropyridin-2-ol

A solution of 2-methoxy-3,6-dimethyl-5-nitropyridine (32.3 g, 182 mmol) from either Part C or D in 12 N hydrochloric acid (300 mL) was heated at 100° C. for 1 h. Analysis by TLC indicated that some starting material remained, so the reaction was heated at 110° C. for an additional 45 min. The reaction mixture was cooled to room temperature and poured onto ice (400 g). When the ice had melted and the temperature of the resulting thick brown suspension was still less than 0° C., the mixture was filtered. The solid cake was washed with water (100 mL) and allowed to dry on the filter for 30 min. The solid was then resuspended in cold (−10° C.) ethanol (150 mL), filtered, washed with cold ethanol (50 mL), and air-dried on the filter for 1 h to afford 3,6-dimethyl-5-nitropyridin-2-ol (28.0 g, 94% yield) as a tan powder: mp 263° C.; $^1$H NMR (400 MHz, DMSO-d$_6$) δ 12.42 (s br, 1H), 8.03 (s, 1H), 2.61 (s, 3 H), 2.01 (s, 3H); LRMS (ESI) m/e 169.3 [(M+H)$^+$, calcd for C$_7$H$_9$N$_2$O$_3$ 169.1].

Part F.
2-(Difluoromethoxy)-3,6-dimethyl-5-nitropyridine

Method A:

Sodium hydride (6.63 g, 166 mmol, 60% in mineral oil) was washed with hexanes (100 mL) to remove the mineral oil and was then suspended in dry acetonitrile (1500 mL) at room temperature. 3,6-Dimethyl-5-nitropyridin-2-ol (27.9 g, 166 mmol) from Part E was added in portions over 30 minutes to give a yellow suspension. During the addition there was some bubbling but negligible temperature change. Cesium fluoride (2.50 g, 16.6 mmol) was then added followed by the slow addition of trimethylsilyl 2-(fluorosulfonyl)difluoroacetate (36.0 mL, 182 mmol) over 30 minutes. During the addition there was some bubbling, the temperature rose from 23° C. to 30° C., and the suspension became noticeably less turbid. After stirring for 15 min, TLC indicated that starting material still remained, so additional trimethylsilyl 2-(fluorosulfonyl) difluoroacetate (6.5 mL, 33 mmol) was added over 10 minutes. After an additional 15 min, TLC indicated consumption of starting material. The reaction was quenched by the addition of water (20 mL) dropwise at such a rate that the bubbling did not become too vigorous. After bubbling ceased, additional water (200 mL) was added. Most of the solvent was removed in vacuo and the aqueous residue was extracted with ethyl acetate (3×200 mL). The combined organic layers were dried over Na$_2$SO$_4$ and evaporated to a brown syrup which solidified upon standing. This residue was dissolved in ethanol (400 mL) and decolorizing charcoal (15 g) was added. The suspension was heated at 70° C. for 20 min and then filtered through a pad of Celite and sand. The filtrate was collected and the solvent was evaporated. The residue was dissolved in methylene chloride and the solution was evaporated to give 2-(difluoromethoxy)-3,6-dimethyl-5-nitropyridine (33.4 g, 92% yield) as a pale yellow solid: mp 51-52° C.; $^1$H NMR (400 MHz, CDCl$_3$) δ 8.21 (s, 1H), 7.55 (t, J=72.0 Hz, 1H), 2.76 (s, 3H), 2.30 (s, 3H).

Method B:

To a suspension of 3,6-methyl-5-nitropyridin-2-ol (700 mg, 4.17 mmol) from Part E in acetonitrile (70 mL) was added NaH (450 mg, 11.3 mmol, 60% in mineral oil). After stirring at room temperature for 15 min, 2,2-difluoro-2-(fluorosulfonyl)acetic acid (0.73 mL, 7.09 mmol) was added dropwise over several minutes. Some bubbling occurred during the addition. After stirring the reaction mixture at room temperature for 15 min, the reaction was quenched by the slow addition of water (10 mL). The acetonitrile was removed in vacuo and the residue was transferred to a separatory funnel containing water (50 mL). The aqueous layer was extracted with EtOAc (3×50 mL). The combined organic layers were washed with brine, dried over MgSO$_4$, filtered and concentrated. The residue was purified by column chromatography on silica gel (10% ethyl acetate in hexanes) to afford 2-(difluoromethoxy)-3,6-dimethyl-5-nitropyridine (870 mg, 96% yield) as a colorless solid identical to that prepared by Method A: mp 48-49° C.; $^1$H NMR (400 MHz, CDCl$_3$) δ 8.21 (s, 1H), 7.54 (t, J=72.4 Hz, 1H), 2.76 (s, 3H), 2.30 (s, 3H); $^{13}$C NMR (100 MHz, CDCl$_3$) δ 158.1, 151.0, 142.0, 137.0, 120.0, 113.9 (t, J=255.8 Hz), 23.5, 14.7.

Part G.
6-(Difluoromethoxy)-2,5-dimethylpyridin-3-amine

To a solution of 2-(difluoromethoxy)-3,6-dimethyl-5-nitropyridine (33.4 g, 153 mmol) from Part F in methylene chloride (100 mL) and ethanol (600 mL) was added 10% palladium on charcoal (3.3 g). The resulting suspension was hydrogenated on a Parr device at 40 psi $H_2$ for 1 h. TLC was used to monitor the reaction. Additional 3.3 g of palladium on charcoal were added hourly until no starting material remained. A total of 13.2 g of Pd/C was added. The reaction mixture was kept under an $H_2$ atmosphere for 2 h after the last addition of catalyst. The reaction mixture was filtered through Celite and sand and the collected solids were washed with ethyl acetate (2×100 mL). The filtrate was concentrated in vacuo to give a grey oil, which was purified by column chromatography on silica gel (35%→50% ethyl acetate in hexanes) to furnish 6-(difluoromethoxy)-2,5-dimethylpyridin-3-amine (25.7 g, 89% yield) as a pale yellow oil which solidified upon cooling in a refrigerator. The product was recrystallized from hexanes below 0° C. to afford white needles: mp 40-42° C.; $^1$H NMR (400 MHz, CDCl$_3$) δ 7.35 (t, J=74.0 Hz, 1H), 6.84 (s, 1H), 2.27 (s, 3H), 2.15 (s, 3H); LRMS (ESI) m/e 189.2 [(M+H)$^+$, calcd for $C_8H_{11}N_2OF_2$ 189.1].

Part H. (S)-5-Chloro-1-(cyclopropyl-2-methoxyethyl)-3-[6-(difluoromethoxy)-2,5-dimethylpyridin-3-ylamino]pyrazin-2(1H)-one (S)-3,5-Dichloro-1-(1-cyclopropyl-2-methoxyethyl)pyrazin-2(1H)-one (15.0 g, 57.01 mmol) from Example 1 Part G and 6-(difluoromethoxy)-2,5-dimethylpyridin-3-amine (10.73 g, 57.01 mmol) from Part G were combined in a 2 L, 3-neck round bottom flask equipped with a thermometer and an addition funnel and placed under $N_2$. THF (570 mL) was added and the mixture was cooled to 0° C. NaHMDS (119.7 mL, 119.7 mmol, 1 M in THF) was added dropwise via the addition funnel over 20 min (the internal temperature was maintained below 5° C.). After the addition was complete, the reaction mixture was stirred at 0° C. for an additional 15 min. The reaction was quenched by the addition of saturated aqueous NH$_4$Cl (60 mL). The mixture was transferred to a separatory funnel containing water (400 mL) and the aqueous layer was extracted with ether (3×300 mL). The combined organic layers were washed with brine, dried over MgSO$_4$, filtered and concentrated. The product was purified by column chromatography on silica gel (30% ethyl acetate in hexanes) to afford (S)-5-chloro-1-(cyclopropyl-2-methoxyethyl)-3-[6-(difluoromethoxy)-2,5-dimethylpyridin-3-ylamino]pyrazin-2(1H)-one (22.14 g, 94% yield) as a pale yellow solid which was subsequently recrystallized from heptane to furnish colorless needles: mp 103.4-104.4° C.; $[\alpha]^{25}_D$ −41.9 (c 0.807, CHCl$_3$); $^1$H NMR (400 MHz, CDCl$_3$) δ 8.42 (s, 1H), 8.02 (s, 1H), 7.46 (t, J=74.0 Hz, 1H), 6.96 (s, 1H), 4.19-4.14 (m, 1H), 3.75 (dd, $J_{AB}$ 10.3, $J_{AX}$=6.3 Hz, 1H), 3.67 (dd, $J_{BA}$=10.3, $J_{BX}$=3.5 Hz, 1H), 3.34 (s, 3H), 2.44 (s, 3H), 2.26 (s, 3H), 1.32-1.26 (m, 1H), 0.81-0.74 (m, 1H), 0.63-0.54 (m, 1H), 0.52-0.47 (m, 1H), 0.36-0.29 (m, 1H); HRMS (ESI) m/e 415.1360 [(M+H)$^+$, calcd for $C_{18}H_{22}N_4O_3ClF_2$ 415.1349].

Part I. (S)-5-Chloro-1-(1-cyclopropyl-2-hydroxyethyl)-3-(6-(difluoromethoxy)-2,5-dimethylpyridin-3-ylamino)pyrazin-2(1H)-one A solution of (S)-5-chloro-1-(cyclopropyl-2-methoxyethyl)-3-[6-(difluoromethoxy)-2,5-dimethylpyridin-3-ylamino]pyrazin-2(1H)-one (2.60 g, 6.27 mmol) from Part H in CH$_2$Cl$_2$ (100 mL) at 0° C. was treated with BBr$_3$ (9.40 mL, 9.40 mmol, 1 M in CH$_2$Cl$_2$) dropwise via syringe while maintaining the temperature below 5° C. After the addition was complete, the reaction mixture was stirred at 0° C. for 1 h. The reaction was quenched by the addition of saturated aqueous NaHCO$_3$. The mixture was then transferred to a separatory funnel containing saturated aqueous NaHCO$_3$ (25 mL). The aqueous layer was extracted with CH$_2$Cl$_2$ (3×50 mL). The combined organic layers were washed with brine, dried over MgSO$_4$, filtered, and concentrated. The product was purified by column chromatography on silica gel (silica gel, 20%→40% ethyl acetate in hexanes) to afford (S)-5-chloro-1-(1-cyclopropyl-2-hydroxyethyl)-3-(6-(difluoromethoxy)-2,5-dimethylpyridin-3-ylamino)pyrazin-2(1H)-one (2.10 g, 84% yield) as an off-white solid: $^1$H NMR (400 MHz, CDCl$_3$) δ 8.39 (s, 1H), 8.00 (s, 1H), 7.46 (t, J=73.8 Hz, 1H), 6.96 (s, 1H), 4.10-4.00 (m, 2H), 3.95 (dd, J=11.8, 7.1 Hz, 1H), 2.44 (s, 3H), 2.26 (s, 3H), 1.82 (br. s., 1H), 1.31-1.22 (m, 1H), 0.87-0.78 (m, 1H), 0.69-0.61 (m, 1H), 0.57-0.50 (m, 1H), 0.37-0.30 (m, 1H); LRMS (ESI) m/e 401.27 [(M+H)$^+$, calcd for $C_{17}H_{20}N_4O_3ClF_2$ 401.12].

Part J. (S)-2-(5-Chloro-3-(6-(difluoromethoxy)-2,5-dimethylpyridin-3-ylamino)-2-oxopyrazin-1(2H)-yl)-2-cyclopropylethyl phenylcarbamate A solution of (S)-5-chloro-1-(1-cyclopropyl-2-methoxyethyl)-3-(6-(difluoromethoxy)-2,5-dimethylpyridin-3-ylamino)pyrazin-2(1H)-one (50 mg, 0.125 mmol) from Part I in THF (3 mL) at 0° C. was treated with NaH (6.3 mg, 0.158 mmol, 60% in mineral oil). The mixture was stirred at 0° C. for 30 min. Phenyl isocyanate (15 μL, 0.315 mmol) was then added and the reaction mixture was stirred at 0° C. for 1 h. The reaction mixture was then quenched by the addition of saturated aqueous NaHCO$_3$ solution. The mixture was transferred to a separatory funnel containing saturated aqueous NaHCO$_3$ solution (5 mL) and the aqueous layer was extracted with EtOAc (3×10 mL). The combined organic layers were washed with brine, dried over MgSO$_4$, filtered, and concentrated. The product was purified by column chromatography on silica gel (25% ethyl acetate in hexanes) to furnish (S)-2-(5-chloro-3-(6-(difluoromethoxy)-2,5-dimethylpyridin-3-ylamino)-2-oxopyrazin-1(21-1)-yl)-2-cyclopropylethyl phenylcarbamate (50 mg, 77% yield) as a colorless amorphous solid: $^1$H NMR (400 MHz, CDCl$_3$) δ 8.37 (s, 1H), 8.02 (s, 1H), 7.55 (t, J=73.8 Hz, 1H), 7.36-7.25 (m, 4H), 7.10-7.01 (m, 1H), 6.85 (s, 1H), 6.68 (br. s., 1H), 4.58 (dd, J=11.8, 4.0 Hz, 1H), 4.48 (dd, J=11.6, 7.6 Hz, 1H), 4.28-4.18 (m, 1H), 2.42 (s, 3H), 2.25 (s, 3H), 1.29-1.19 (m, 1H), 0.84 (tt, J=8.4, 5.3 Hz, 1H), 0.70-0.54 (m, 2H), 0.42-0.34 (m, 1H); HRMS (ESI) m/e 520.1561 [(M+H), calcd for $C_{24}H_{25}N_5O_4ClF_2$ 520.1563].

Example 15

(S)-2-(5-Chloro-3-(6-(difluoromethoxy)-2,5-dimethylpyridin-3-ylamino)-2-oxopyrazin-1(2H)-yl)-2-cyclopropylethyl pyridin-3-ylcarbamate

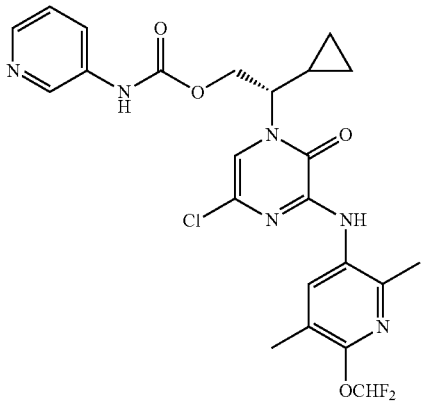 [SMILES: Cc1cc(Nc2nc(Cl)cn([C@H](COC(=O)Nc3cccnc3)C3CC3)c2=O)c(C)nc1OC(F)F]

Prepared by the method described in Example 14 using the appropriate starting materials to give the desired product as a colorless solid: $^1$H NMR (500 MHz, CDCl$_3$) δ 8.44 (br. s., 1H), 8.30 (s, 1H), 8.25 (d, J=3.7 Hz, 1H), 8.00 (s, 3H), 7.44 (t, J=73.5 Hz, 1H), 7.26-7.21 (m, 1H), 6.86 (s, 1H), 4.58 (dd, J=11.9, 3.7 Hz, 1H), 4.49 (dd, J=11.6, 7.9 Hz, 1H), 4.27 (t, J=6.9 Hz, 1H), 2.37 (s, 3H), 2.23 (s, 3H), 1.30-1.18 (m, 1H), 0.89-0.80 (m, 1H), 0.69-0.61 (m, 1H), 0.58 (dq, J=9.6, 4.8 Hz, 1H), 0.41-0.33 (m, 1H); LRMS (ESI) m/e 521.31 [(M+H)$^+$, calcd for C$_{23}$H$_{24}$N$_6$O$_4$ClF$_2$ 521.15].

It will be evident to one skilled in the art that the present disclosure is not limited to the foregoing illustrative examples, and that it can be embodied in other specific forms without departing from the essential attributes thereof. It is therefore desired that the examples be considered in all respects as illustrative and not restrictive, reference being made to the appended claims, rather than to the foregoing examples, and all changes which come within the meaning and range of equivalency of the claims are therefore intended to be embraced therein.

We claim:
1. A compound of Formula I

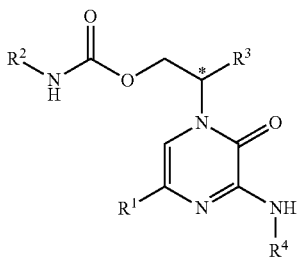

where:
R$^1$ is hydrogen, halo, cyano, or alkyl;
R$^2$ is alkyl or haloalkyl;
or R$^2$ is phenyl, pyridinyl, pyrimidinyl, pyridazinyl, or triazinyl, and is substituted with 0-3 substituents independently selected from the group consisting of halo, cyano, alkyl, alkoxy, haloalkyl, and haloalkoxy;
R$^3$ is hydrogen, alkyl, alkenyl, alkynyl, cycloalkyl, (cycloalkyl)alkyl, haloalkyl, alkoxyalkyl, or (haloalkoxy)alkyl;
R$^4$ is phenyl, pyridinyl, pyrimidinyl, pyridazinyl, or triazinyl and is substituted with 0-3 substituents independently selected from the group consisting of halo, alkyl, alkoxy, haloalkyl, and haloalkoxy; and
the carbon bearing the asterisk is of the (R) or (S) configuration;
or a pharmaceutically acceptable salt thereof.

2. A compound of claim 1 where R$^1$ is halo or cyano; R$^2$ is alkyl or is pyridinyl substituted with 0-3 substituents independently selected from the group consisting of halo, cyano, alkyl, and alkoxy; R$^3$ is cycloalkyl; R$^4$ is pyridinyl substituted with 0-3 substituents independently selected from the group consisting of alkyl, alkoxy, and haloalkoxy; and the carbon bearing the asterisk is of the (S) configuration; or a pharmaceutically acceptable salt thereof.

3. A compound of claim 2 where R$^1$ is chloro or cyano; R$^2$ is ethyl, propyl, butyl, pyridinyl, (methyl)(methoxy)pyridinyl, (dimethyl)(methoxy)pyridinyl, or (dimethyl)(ethoxy)pyridinyl; R$^3$ is cyclopropyl; R$^4$ is (dimethyl)(methoxy)pyridinyl or (dimethyl)(difluoromethoxy)pyridinyl; and the carbon bearing the asterisk is of the (S) configuration; or a pharmaceutically acceptable salt thereof.

4. A compound of claim 1 where R$^1$ is hydrogen, chloro, bromo, cyano, or methyl.

5. A compound of claim 1 where R$^2$ is alkyl.

6. A compound of claim 1 where R$^2$ is phenyl or pyridinyl and is substituted with 0-3 substituents independently selected from halo, cyano, alkyl, alkoxy, haloalkyl, and haloalkoxy.

7. A compound of claim 1 where R$^3$ is alkyl, cycloalkyl, or alkoxyalkyl.

8. A compound of claim 1 where R$^3$ is cyclopropyl.

9. A compound of claim 1 where R$^4$ is pyridinyl and is substituted with 0-3 substituents independently selected from alkyl, alkoxy, and haloalkoxy.

10. A compound of claim 1 where the carbon bearing the asterisk is of the (S) configuration.

11. A compound of claim 1 selected from the group consisting of
(S)-2-(5-Chloro-3-(6-methoxy-2,5-dimethylpyridin-3-ylamino)-2-oxopyrazin-1(2H)-yl)-2-cyclopropylethyl pyridin-3-ylcarbamate;
(S)-2-(5-Chloro-3-(6-methoxy-2,5-dimethylpyridin-3-ylamino)-2-oxopyrazin-1(2H)-yl)-2-cyclopropylethyl 6-ethoxy-2,5-dimethylpyridin-3-ylcarbamate;
(S)-2-(5-Chloro-3-(6-methoxy-2,5-dimethylpyridin-3-ylamino)-2-oxopyrazin-1(2H)-yl)-2-cyclopropylethyl 6-methoxy-2,5-dimethylpyridin-3-ylcarbamate;
(S)-2-(5-Chloro-3-(6-methoxy-2,5-dimethylpyridin-3-ylamino)-2-oxopyrazin-1(2H)-yl)-2-cyclopropylethyl 6-methoxy-2-methylpyridin-3-ylcarbamate;
(S)-2-(5-Chloro-3-(6-(difluoromethoxy)-2,5-dimethylpyridin-3-ylamino)-2-oxopyrazin-1(2H)-yl)-2-cyclopropylethyl phenylcarbamate;
(S)-2-(5-Chloro-3-(6-(difluoromethoxy)-2,5-dimethylpyridin-3-ylamino)-2-oxopyrazin-1(2H)-yl)-2-cyclopropylethyl pyridin-3-ylcarbamate;
(S)-2-(5-Chloro-3-(6-methoxy-2,5-dimethylpyridin-3-ylamino)-2-oxopyrazin-1(2H)-yl)-2-cyclopropylethyl phenylcarbamate;

(S)-2-(5-Chloro-3-(6-methoxy-2,5-dimethylpyridin-3-ylamino)-2-oxopyrazin-1(2H)-yl)-2-cyclopropylethyl 3-cyanophenylcarbamate;

(S)-2-(5-Chloro-3-(6-methoxy-2,5-dimethylpyridin-3-ylamino)-2-oxopyrazin-1(2H)-yl)-2-cyclopropylethyl 2-chlorophenylcarbamate;

(S)-2-(5-Chloro-3-(6-methoxy-2,5-dimethylpyridin-3-ylamino)-2-oxopyrazin-1(2H)-yl)-2-cyclopropylethyl 4-chlorophenylcarbamate;

(S)-2-(5-Chloro-3-(6-methoxy-2,5-dimethylpyridin-3-ylamino)-2-oxopyrazin-1(2H)-yl)-2-cyclopropylethyl 3,5-dichlorophenylcarbamate; and (S)-2-(5-Chloro-3-(6-methoxy-2,5-dimethylpyridin-3-ylamino)-2-oxopyrazin-1(2H)-yl)-2-cyclopropylethyl 2,4-dichlorophenylcarbamate;

or a pharmaceutically acceptable salt thereof.

12. A pharmaceutical composition comprising a compound of claim 1, or a pharmaceutically acceptable salt thereof, and a pharmaceutically acceptable carrier.

\* \* \* \* \*